(12) United States Patent
Manfredi

(10) Patent No.: US 6,551,786 B2
(45) Date of Patent: Apr. 22, 2003

(54) SCREEN ASSAY FOR SELECTING PROTEIN-PROTEIN INTERACTION MODULATORS

(75) Inventor: John Manfredi, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 10/040,967

(22) Filed: Jan. 4, 2002

(65) Prior Publication Data

US 2002/0106632 A1 Aug. 8, 2002

Related U.S. Application Data

(60) Provisional application No. 60/259,759, filed on Jan. 4, 2001.

(51) Int. Cl.$^7$ .................. G01N 33/567; G01N 33/569; C07H 21/04; C12N 1/14; C12N 15/00
(52) U.S. Cl. ................... 435/6; 435/4; 435/7.1; 435/7.31; 435/69.1; 435/69.7; 435/69.9; 435/471; 435/476; 435/481; 435/483; 435/320.1; 435/243; 435/252.3; 435/254.1; 435/255.1; 536/23.1; 536/23.4
(58) Field of Search .................. 435/4, 6, 7.1, 7.2, 435/7.31, 7.4, 29, 34, 69.1, 69.7, 69.9, 71.1, 71.2, 471, 476, 480, 481, 483, 243, 254.1, 252.3, 255.1, 320.1; 536/22.1, 23.1, 23.2, 23.4, 24.1

(56) References Cited

U.S. PATENT DOCUMENTS

| | | | | |
|---|---|---|---|---|
| 5,637,463 A | * | 6/1997 | Dalton et al. | 435/320.1 |
| 5,695,941 A | * | 12/1997 | Brent et al. | 435/254.21 |
| 5,834,247 A | | 11/1998 | Comb et al. | |
| 5,885,779 A | * | 3/1999 | Sadowski et al. | 435/254.2 |
| 5,981,182 A | | 11/1999 | Jacobs, Jr. et al. | |
| 6,057,091 A | | 5/2000 | Beachy et al. | |
| 6,294,330 B1 | * | 9/2001 | Michnick et al. | 435/252.3 |
| 6,365,347 B1 | * | 4/2002 | Murray et al. | 435/320.1 |

OTHER PUBLICATIONS

Ozawa, T., et al. A Fluorescent Indicator for Detecting Protein–Protein Interactions in Vivo Based on Protein–Splicing. Anal. Chem. 72, p. 5151–5157 (2000).*
Remy, I. and Michnik, S. W. Clonal selection and in vivo quantitation of protein interactions with protein–fragment complementation assays. Proc. Natl. Acad. Sci. USA 96, p. 5394–5399 (1999).*
Karimova, et al. A bacterial two–hybrid system based on a reconstituted signal transduction pathway. Proc. Natl. Acad. Sci. USA 95, p. 5752–5756 (1998).*
U.S. patent application Ser. No. 10/040,910, Manfredi, filed Jan. 4, 2002.
U.S. patent application Ser. No. 10/040,969, Manfredi, filed Jan. 4, 2002.
U.S. patent application Ser. No. 10/040,964, Manfredi et al., filed Jan. 4, 2002.
Chong, Shaorong, et al., "Protein Splicing Involving the Saccharomyces cerevisiae VMA Intein", *The Journal of Biological Chemistry*, Sep. 6, 1996; 271(36):22159–22168.
Wu, Hong, et al., "Protein trans–splicing and functional mini–inteins of a cyanobacterial dnaB intein", *Biochimica et Biophysica Acta*, 1998; 1387:422–432.
Shingledecker, Kaori, et al., "Molecular dissection of the Mycobacterium tuberculosis RecA intein: design of a minimal intein and of a trans–splicing system involving two intein fragments", *Gene*, 1998; 207:187–195.
Severinov, Konstantin, et al., "Expressed Protein Ligation, a Novel Method for Studying Protein–Protein Interactions in Transcription", *The Journal of Biological Chemistry*, Jun. 26, 1998; 273(26):16205–16209.
Wu, Hong, et al., "Protein trans–splicing by a split intein encoded in a split DnaE gene of Synechocystis sp. PCC6803", *Proc. Natl. Acad. Sci. USA*, Aug. 1998; 95:9226–9231.
Lew, Belinda M., et al., "Characteristics of Protein Splicing in trans Mediated by a Semisynthetic Split Intein", *Biopolymers*, 1999; 51:355–362.
Xu, Rong, et al., "Chemical ligation of folded recombinant proteins: Segmental isotopic labeling of domains for NMR studies", *Proc. Natl. Acad. Sci. USA*, Jan. 1999; 96:388–393.
Evans, Thomas C., Jr., et al., "The in Vitro Ligation of Bacterially Expressed Proteins Using an Intein from Methanobacterium thermoautotrophicum", *The Journal of Biological Chemistry*, Feb. 12, 1999; 274(7):3923–3926.
Amitai, Gil, et al., "Fine–tuning an engineered intein", *Nature Biotechnology*, Sep. 1999; 17:854–855.
Evans, Thomas C., Jr., et al., "Protein trans–Splicing and Cyclization by Naturally Split Intein from the dnaE Gene of Synechocystis Species PCC6803", *The Journal of Biological Chemistry*, Mar. 31, 2000; 275(13):9091–9094.
Ozawa, Takeaki, et al., "A Fluorescent Indicator for Detecting Protein–Protein Interactions in Vivo Based on Protein Splicing", *Analytical Chemistry*, Nov. 1, 2000; 72(21):5151–5157.
Ozawa, Takeaki, et al., "Split Luciferase as an Optical Probe for Detecting Protein–Protein Interactions in Mammalian Cells Based on Protein Splicing", *Analytical Chemistry*, Jun. 1, 2001; 73(11):2516–2521.

* cited by examiner

Primary Examiner—David Guzo
Assistant Examiner—David A. Lambertson
(74) Attorney, Agent, or Firm—Jay Z. Zhang; Myriad IP Dept.

(57) ABSTRACT

A method for selecting compounds capable of modulating protein-protein interactions is provided, in which two fusion proteins are prepared and allowed to interact with each other in the presence of test compounds. The interaction between the two fusion proteins leads to protein trans-splicing, producing an active reporter. Compounds that disrupt or enhance protein-protein interactions can be selected based on the presence or absence of the active reporter.

26 Claims, 17 Drawing Sheets

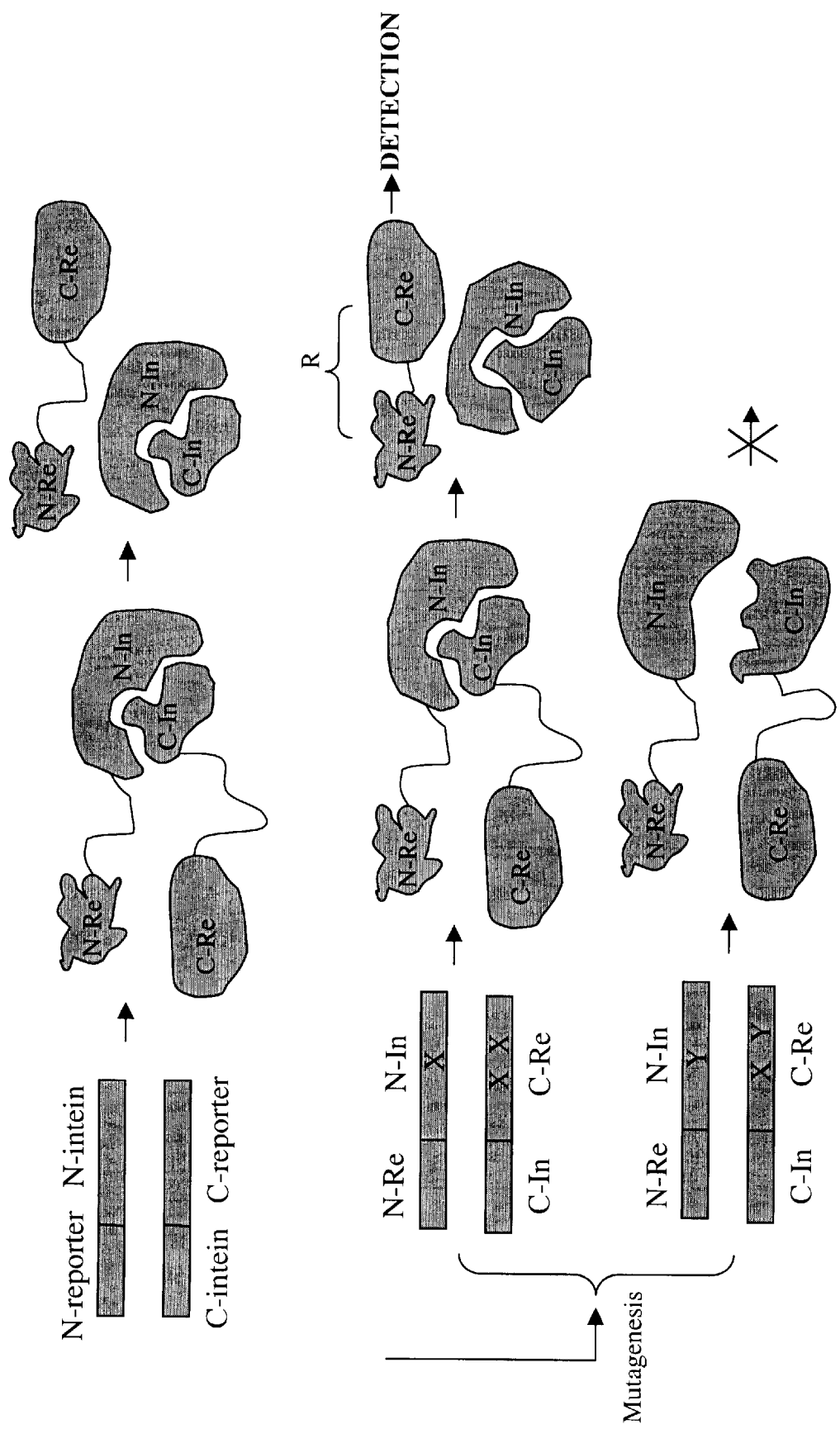
Figure 2A Selecting Non-interacting N-intein & C-intein

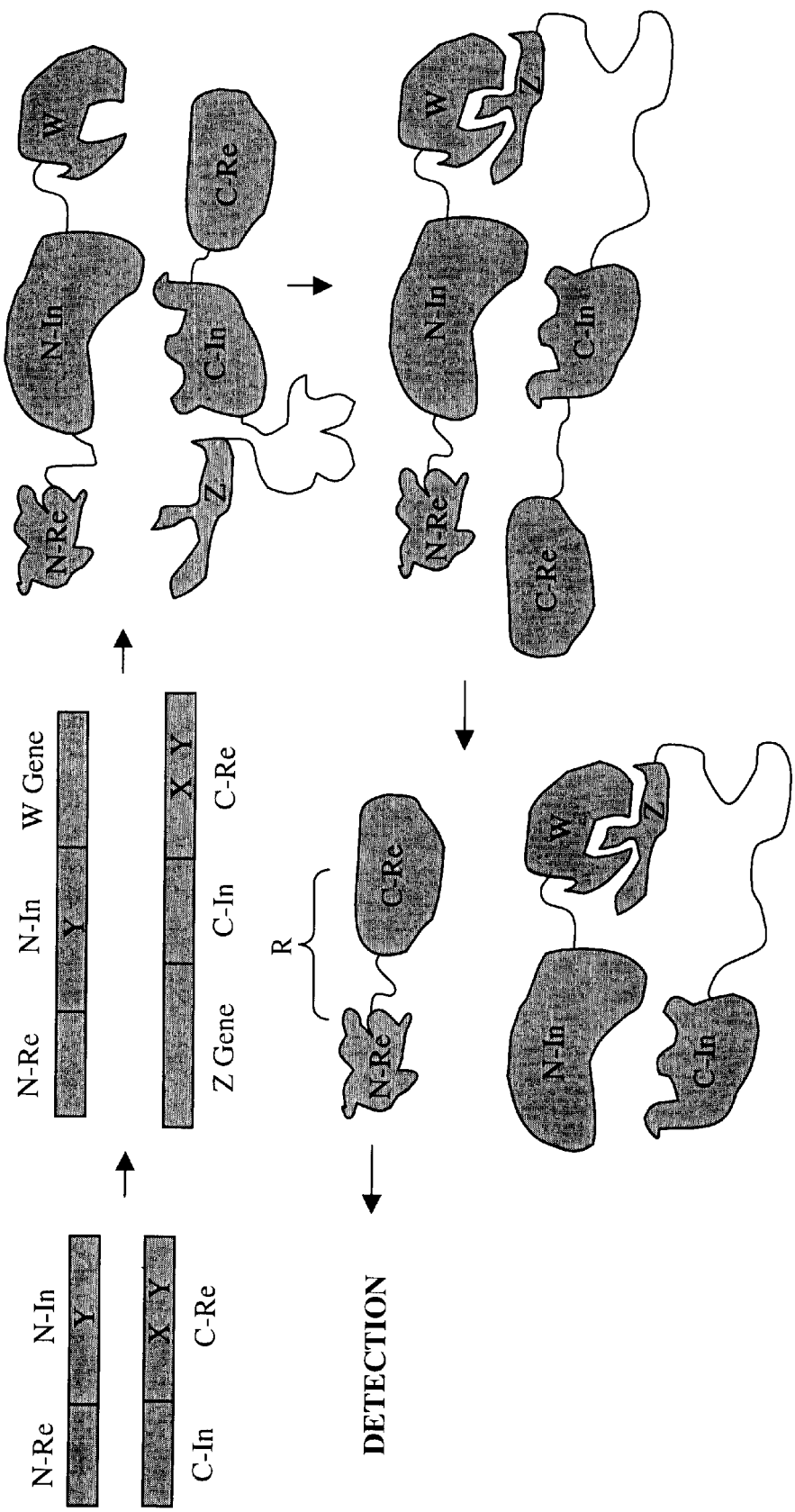
Figure 2B  Verifying That the Selected Non-interacting N-intein & C-intein Are Capable of Mediating Protein Splicing Figure 6 Intein-Based Multi-Hybrid System Figure 7 Detecting Extracellular Protein-Protein Interaction Figure 8 Detecting Interaction between Intracellular and Membrane Proteins

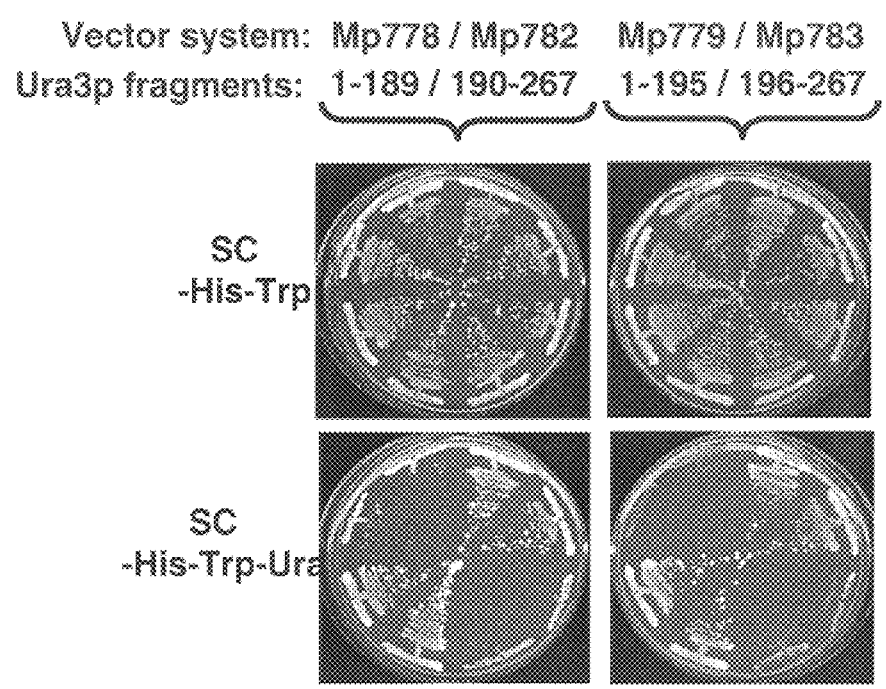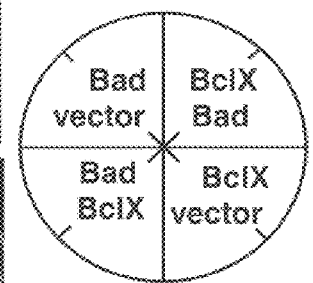
Figure 10

SCREEN ASSAY FOR SELECTING PROTEIN-PROTEIN INTERACTION MODULATORS

RELATED APPLICATIONS

This application claims priority from U.S. Provisional Application No. 60/259,759 filed on Jan. 4, 2001, which is incorporated herein by reference in its entirety.

FIELD OF THE INVENTION

The present invention generally relates to methods for identifying pharmaceutically relevant compounds, and particularly to methods for selecting compounds capable of modulating protein-protein interactions.

BACKGROUND OF THE INVENTION

There has been much interest in protein-protein interactions in the field of proteomics. A number of biochemical approaches have been used to identify interacting proteins. These approaches generally employ the affinities between interacting proteins to isolate proteins in a bound state. Examples of such methods include coimmunoprecipitation and copurification, optionally combined with cross-linking to stabilize the binding. Identities of the isolated protein interacting partners can be characterized by, e.g., mass spectrometry. See e.g., Rout et al., *J. Cell. Biol.,* 148:635–651 (2000); Houry et al., *Nature,* 402:147–154 (1999); Winter et al., *Curr. Biol.,* 7:517–529 (1997). A popular approach useful in large-scale screening is the phage display method, in which filamentous bacteriophage particles are made by recombinant DNA technologies to express a peptide or protein of interest fused to a capsid or coat protein of the bacteriophage. A whole library of peptides or proteins of interest can be expressed and a bait protein can be used to screening the library to identify peptides or proteins capable of binding to the bait protein. See e.g., U.S. Pat. Nos. 5,223,409; 5,403,484; 5,571,698; and 5,837,500. Notably, the phage display method only identifies those proteins capable of interacting in an in vitro environment, while the coimmunoprecipitation and copurification methods are not amenable to high throughput screening.

The yeast two-hybrid system is a genetic method that overcomes certain shortcomings of the above approaches. The yeast two-hybrid system has proven to be a powerful method for the discovery of specific protein interactions in vivo. See generally, Bartel and Fields, eds., *The Yeast Two-Hybrid System,* Oxford University Press, New York, N.Y., 1997. The yeast two-hybrid technique is based on the fact that the DNA-binding domain and the transcriptional activation domain of a transcriptional activator contained in different fusion proteins can still activate gene transcription when they are brought into proximity to each other. As shown in FIG. 1, in a yeast two-hybrid system, two fusion proteins are expressed in yeast cells. One has a DNA-binding domain of a transcriptional activator fused to a test protein. The other, on the other hand, includes a transcriptional activating domain of the transcriptional activator fused to another test protein. If the two test proteins interact with each other in vivo, the two domains of the transcriptional activator are brought together reconstituting the transcriptional activator and activating a reporter gene controlled by the transcriptional activator. See, e.g., U.S. Pat. No. 5,283,173.

Because of its simplicity, efficiency and reliability, the yeast two-hybrid system has gained tremendous popularity in many areas of research. Numerous protein-protein interactions have been identified using the yeast two-hybrid system. The identified proteins have contributed significantly to the understanding of many signal transduction pathways and other biological processes. For example, the yeast two-hybrid system has been successfully employed in identifying a large number of novel cell cycle regulators that are important in complex cell cycle regulations. Using known proteins that are important in cell cycle regulation as baits, other proteins involved in cell cycle control were identified by virtue of their ability to interact with the baits. See generally, Hannon et al., in *The Yeast Two-Hybrid System,* Bartel and Fields, eds., pages 183–196, Oxford University Press, New York, N.Y., 1997. Examples of cell cycle regulators identified by the yeast two-hybrid system include CDK4/CDK6 inhibitors (e.g., p16, p15, p18 and p19), Rb family members (e.g., p130), Rb phosphatase (e.g., PP1-α2), Rb-binding transcription factors (e.g., E2F-4 and E2F-5), General CDK inhibitors (e.g., p21 and p27), CAK cyclin (e.g., cyclin H), and CDK Thr161 phosphatase (e.g., KAP and CDI1). See id. "[T]he two-hybrid approach promises to be a useful tool in our ongoing quest for new pieces of the cell cycle puzzle." See id at page 193. In another example, the yeast two-hybrid system proved to be a powerful approach in analyzing the yeast pheromone response pathway, a complex multistep signal transduction process in haploid yeast cell mating. See generally, Sprague et al., in *The Yeast Two-Hybrid System,* Bartel and Fields, eds., pages 173–182, Oxford University Press, New York, N.Y., 1997. As described in Sprague, various genes were isolated from mutant yeast strains having altered pheromone response patterns. However, it was not clear how the proteins encoded by these genes function in the pheromone response pathway. The yeast two-hybrid system was utilized to test such proteins and mutant forms thereof for their ability to interact with each other. As a result, new insights and better understandings of the complex process were achieved. See id.

Reverse two-hybrid systems have also been developed based the yeast two-hybrid systems and are disclosed in, e.g., U.S. Pat. Nos. 5,525,490; 5,733,726; 5,885,779; Vidal et al., *Proc. Natl. Acad. Sci. USA,* 93:10315–10320 (1996); and Vidal et al., *Proc. Natl. Acad. Sci. USA,* 93:10321–10326 (1996). Such reverse two-hybrid systems can be useful in identifying and selecting compounds capable of modulating a particular protein-protein interaction.

However, such reverse two-hybrid systems in the art typically depend on gene activation in the nucleus of host cells and has generally required that specific protein-protein interactions between fusion proteins occur within the nucleus of host cells. Thus, although certain conventional reverse yeast two-hybrid systems have been used successfully in identifying compounds capable of modulating protein-protein interactions, their usefulness may be limited when it is used in the context of protein-protein interactions that require non-nuclear environment. For example, traditional transcription-based reverse two-hybrid systems are not applicable to interactions between transcriptional factors. In addition, many cell surface proteins and their ligands contain disulfide bonds, which can be disrupted under the intracellular reducing conditions. Additionally, posttranslational protein modifications, particularly glycosylation, typically would preclude the nuclear localization of the modified proteins.

Cytosolic and cell surface protein-protein interactions play major roles in normal cellular functions and biological responses. In particular, many cytosolic and cell surface protein-protein interactions are involved in disease pathways. For example, attacks by pathogens such as viruses and bacteria on mammalian cells typically begin with interactions between viral or bacterial proteins and mammalian cell surface proteins. In addition, many protein-protein interactions between factors in the transcriptional machineries are also valuable drug targets. Therefore, there is a need in the art for improved methods that can be used to identify compounds capable of modulating such protein-protein interactions.

SUMMARY OF THE INVENTION

This invention provides a versatile and sensitive assay system for detecting protein-protein interactions that circumvents the above-described limitations inherent in prior art methods. Particularly, the present invention utilizes the so-called inteins, which are peptide sequences capable of directing protein trans-splicing both in vivo and in vitro. An intein is an intervening protein sequence in a protein precursor that is excised from the protein precursor during protein splicing. Protein splicing results in the concomitant ligation of the flanking protein fragments, i.e., the exteins, with a native peptide bond, thus forming a mature extein protein and the free intein. It is now known that inteins incorporated into non-native precursors can also cause protein-splicing and excision of the inteins. In addition, an N-terminal intein fragment in a fusion protein and a C-terminal intein fragment in another fusion protein, when brought into contact with each other, can bring about trans-splicing between the two fusion proteins. Thus, in accordance with the present invention, two hybrid fusion constructs are provided. One has a first test agent and an N-terminal intein fragment or N-intein, and the other has a second test agent and a C-terminal intein fragment or C-intein. In addition, one or both fusion constructs may have a reporter that undergoes detectable changes upon trans-splicing of the fusion constructs. If the first and second test agents interact with each other, thus bringing the N-intein and C-intein to close proximity, protein trans-splicing takes place. As a result, the fusion constructs are spliced, causing detectable changes in the reporter. Thus, by detecting the changes in the reporter, interactions between two test agents can be determined.

Intein-based trans-splicing can take place in vitro in a cell free environment. Therefore, the assay system of the present invention can be used for convenient and speedy in vitro analysis of protein-protein interactions. Particularly, the system can be easily adapted to high-throughput screening procedures.

In addition, trans-splicing can also occur inside a host cell in many different cellular backgrounds and compartments. In particular, unlike the traditional two-hybrid systems, the interacting proteins need not be transported into the cell nucleus. Thus, the system is useful in determining protein-protein interactions that require a specific cellular environment. For example, the system can be employed to detect interactions between nuclear proteins, between cytosolic proteins, and between membrane or extracellular proteins.

Additionally, protein trans-splicing mediated by the N-intein and C-intein is independent of other cellular factors and does not require the action of additional proteins such as proteases. This makes the assay system of the present invention more reliable and easier to perform as compared to the assay methods known in the art for detecting protein-protein interactions.

Another distinct feature of the intein-based assay is that the detection of protein-protein interaction is based on the occurrence of protein trans-splicing events, which typically are associated with protein cleavage and result in new protein structures and functions. Thus, the intein-based assay is well-suited to exploit the numerous direct and indirect methods available in the art for detecting changes in protein structures and functions. Because the intein-based assay can accommodate these numerous detection methods, there is great flexibility in choosing methods that are optimal for a particular condition.

Accordingly, in accordance with a first aspect of the present invention, a method for detecting protein-protein interaction is provided. Briefly, two fusion proteins are prepared and allowed to interact with each other. One of the two fusion proteins includes an N-intein and a first test polypeptide, and the other fusion protein includes a C-intein and a second test polypeptide. One or both of the two fusion proteins have an inactive reporter capable of being converted to an active reporter upon trans-splicing through the N-intein and the C-intein. The change in the active reporter level is determined. An increase in the amount of the active reporter would indicate that the first and second test polypeptides interact with each other through, e.g., binding affinity, to result in the trans-splicing of the two fusion proteins mediated by the N-intein and the C-intein. Preferably, the N-intein and C-intein are not associated with each other and do not exhibit any significant binding affinity to each other. Nor do they associate with or bind to the inactive reporter or test polypeptides in the fusion proteins.

In one embodiment, the inactive reporter can be a polypeptide linked to one of the fusion proteins, and is cleaved off into a free form from the fusion protein upon protein trans-splicing. The reporter polypeptide can be selected and the fusion proteins can be designed such that the precursor form of the polypeptide is inactive while the free reporter released from the fusion protein is active, i.e., is detectable directly or indirectly.

In another embodiment, one of the two fusion proteins has a nonfunctional portion of a reporter polypeptide linked to the N-terminus of the N-intein. The other fusion protein comprises a distinct but similarly nonfunctional portion of the same reporter polypeptide linked to the C-terminus of the C-intein. Upon trans-splicing between the two fusion proteins through the N- and C-inteins, the two inactive reporter polypeptides are ligated together with a peptide bond, thereby forming an active reporter protein, which is detectable directly or indirectly.

The assay can be conducted in vitro in a substantially cell free environment by mixing together purified forms of the two fusion proteins under conditions suitable for protein interactions and for protein trans-splicing. Alternatively, the fusion proteins can be recombinantly expressed separately in different host cells, and cell lysates or crude extracts prepared from the cells can be mixed to allow protein-protein interaction. The active reporter protein is then detected.

The assay can also be conducted in vivo by allowing the fusion proteins to interact within a host cell. Suitable cells include, but are not limited to, bacteria cells, yeast cells, plant cells, insect cells and animal cells. Chimeric genes encoding the above-described fusion proteins are introduced into a host cell to express recombinantly the fusion proteins. The amount of the active reporter protein in the host cell is determined. In one embodiment, a first chimeric gene encoding one of the two fusion proteins is expressed in a haploid Saccharomyces cell of a mating type and a second chimeric gene encoding the other fusion protein is expressed in a haploid Saccharomyces cell of mating type α. The two cells are mated to form a diploid cell, and any change in the amount of the active reporter protein in the diploid is then determined.

In a specific embodiment of the in vivo assay, expression of one or more of the chimeric genes can be made inducible, e.g., by placing the genes under control of an inducible promoter, such that one or more of the fusion proteins are produced when the host cell is subject to a predetermined condition.

In yet another embodiment of the in vivo assay, the fusion proteins can have a signal peptide and optionally a membrane anchoring domain such that the fusion proteins recombinantly expressed in the host cells are secreted extracellularly or anchored on cell surface.

In addition, the assay can also be conducted in the presence of a third polypeptide. In this manner, the interaction between the first and second test polypeptides can be detected if the interaction requires the presence of the third polypeptide. The third polypeptide may be a protein having affinity to either the first or second test polypeptides or both. Alternatively, the third polypeptide can modify one or both test polypeptides, e.g., by phosphorylation, glycosylation, and the like.

The techniques used for monitoring the occurrence of protein trans-splicing events and detecting an active reporter will depend on the inactive reporter used and the active reporter derived therefrom. The system of the present invention can be designed such that an active reporter can be detected based on changes in protein sizes or other properties, or activation of certain protein functions. For example, in an in vivo system, detection of an active reporter can be based on cell viability assays, color assays, and the like.

In accordance with a second aspect of the present invention, the above-described assay system is employed to determine whether a compound is capable of interfering with an interaction between a first polypeptide and a second polypeptide. Essentially, two fusion proteins as described above are provided except that the first and second polypeptides are known to interact with each other. The interaction between the two fusion proteins in the presence of the test compound is determined. Many suitable reporters can be used in this screening assay system. Preferably, a reverse or negative selection technique is incorporated into the screening assay of the present invention. For example, the fusion proteins can be designed such that the active reporter generated by protein trans-splicing is toxic to the host cell or represses the expression of a detectable gene. In this manner, compounds capable of interfering with the interaction between the two fusion proteins can be identified based on, e.g., the survival of the host cell or the expression of a detectable gene.

In accordance with another aspect of the present invention, a composition for detecting protein-protein interactions is provided, which includes a first chimeric gene encoding a first fusion protein and a second chimeric gene encoding a second fusion protein. The first fusion protein includes an N-intein and a first test polypeptide. The second fusion protein has a C-intein and a second test polypeptide. One or both of the fusion proteins has an inactive reporter protein capable of being converted to an active reporter protein upon trans-splicing through the N-intein and the C-intein. In one embodiment, each of the chimeric genes is contained in an expression vector, respectively. The expression vectors also contain elements necessary for the replication of the vector in a host cell, the correct transcription and translation of the chimeric genes (e.g., promoters and other transcriptional regulatory elements, transcription termination signal, etc.). The vectors preferably also contain a selection marker gene for selecting those host cells harboring the expression vectors. Preferably, the N-intein and the C-intein are incapable of interacting with each other or with the inactive reporter.

The foregoing and other advantages and features of the invention, and the manner in which the same are accomplished, will become more readily apparent upon consideration of the following detailed description of the invention taken in conjunction with the accompanying examples and drawings, which illustrate preferred or exemplary embodiments.

BRIEF DESCRIPTION OF THE DRAWINGS

FIG. 2A illustrates a genetic selection process for selecting N-inteins and C-inteins that do not interact with each other;

FIG. 2B shows a process for verifying that the selected non-interacting N-intein and C-intein are capable of mediating protein trans-splicing;

FIG. 10 shows some successful testing results of the intein-based two-hybrid systems demonstrated in the Example;

DETAILED DESCRIPTION OF THE INVENTION

Figure 1:
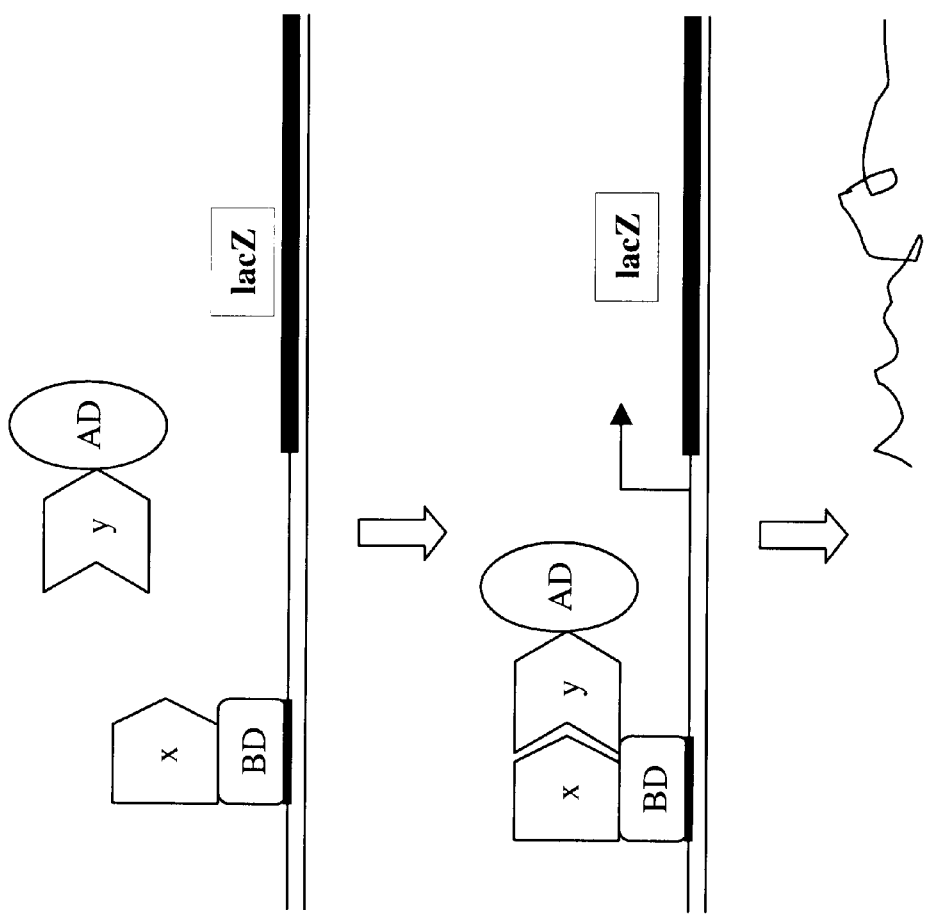
FIG. 1 is an illustration of the classic yeast two-hybrid system known in the art.

The term "compound" as used herein encompasses all types of organic or inorganic molecules, including but not limited to proteins, peptides, polysaccharides, lipids, nucleic acids, small organic molecules, inorganic compounds, and derivatives thereof.

As used herein, the terms "polypeptide," "protein," and "peptide" are used interchangeably to refer to amino acid chains in which the amino acid residues are linked by covalent peptide bonds. The amino acid chains can be of any length of at least two amino acids, including full-length proteins. Unless otherwise specified, the terms "polypeptide," "protein," and "peptide" also encompass various modified forms thereof, including but not limited to glycosylated forms, phosphorylated forms, etc.

The term "test agent" means a chemical compound, preferably an organic compound, to be tested in the present invention to determine its ability to interact with another chemical compound. Test agents may include various forms of organic compounds, or combinations or conjugates thereof. In one embodiment, the test agents preferably are polypeptides, in which case the test agents are termed "test polypeptides" or "test proteins."

The term "fusion construct" refers to a non-naturally occurring hybrid or chimeric construct having two or more distinct portions covalently linked together, each portion being or being derived from a specific molecule. When two or more portions in a fusion construct as defined above are polypeptides and are linked together by peptide bonds, the fusion construct is conveniently referred to as "fusion protein."

As used herein, the term "interacting" or "interaction" means that two domains or independent entities exhibit sufficient physical affinity to each other so as to bring the two "interacting" domains or entities physically close to each other. An extreme case of interaction is the formation of a chemical bond that results in continual, stable proximity of the two domains. Interactions that are based solely on physical affinities, although usually more dynamic than chemically bonded interactions, can be equally effective at co-localizing independent entities. Examples of physical affinities and chemical bonds include but are not limited to, forces caused by electrical charge differences, hydrophobicity, hydrogen bonds, van der Wals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include specific interactions between antigen and antibody, ligand and receptor, and the like.

As used in the present disclosure, the term "reporter" means a molecule or a moiety or domain thereof that can be used as a marker for the determination of the occurrence of protein trans-splicing. An "inactive reporter" is a form of the reporter that is not detectable by a particular detection means, while an "active reporter" is a form of the reporter that is detectable by that detection means. It should be recognized that the terms "detectable" and "not detectable" are used herein in a relative sense. In essence, there should be a measurable or detectable change in the reporter, either quantitative or qualitative, upon intein-based trans-splicing. For purposes of the present discussion, "active reporters" include both reporters that are directly detectable and those reporters that are detectable indirectly. One example of an indirectly detectable active reporter is a transcription activator that can activate the transcription of a detectable gene and thus cause the synthesis of a detectable protein encoded by the detectable gene.

Many reporters are known in the art and the selection and application of any of those reporters to the present invention should be apparent to a skilled artisan apprised of the present disclosure. Examples of reporters suitable for use in a yeast system or other systems include, but are not limited to: β-galactosidase (β-Gal) encoded by the LacZ gene which converts white X-Gal into a product with a blue color; the product of the CYH2 gene, which confers sensitivity to cycloheximide (CYH); proteins encoded by the auxotrophic genes URA3, HIS3, LEU2, and TRP1; and green fluorescent protein (GFP), which can be sorted by flow-activated cell sorting (FACS). See Cubitt et al., *Trends Biochem. Sci.*, 20:448–455 (1995).

Typically, an inactive reporter can be converted to an active reporter upon trans-splicing in the method of this invention. For example, a molecule when fused to a construct of the present invention may not be detectable and thus is referred to as "an inactive reporter." The fused form may be released from the fusion construct into a free form of the molecule that is detectable. This detectable free form is referred to as an "active reporter," which is in contrast to the "inactive" undetectable bound form of the reporter. In another example, two inactive reporters are fused to an N-intein and a C-intein, respectively, and upon trans-splicing, the two inactive reporters are ligated together forming a detectable active reporter. For this purpose, fragments of an active reporter that are not detectable can also be referred to "inactive reporter." Thus, an N-terminal fragment of a reporter protein is fused to an N-intein and a C-terminal fragment of the reporter protein is fused to a C-intein. Upon protein trans-splicing mediated by the N- and C-intein, the N-terminal and C-terminal fragments can be ligated, thereby forming a full-length detectable active reporter protein.

As is known in art, inteins are intervening protein sequences in protein precursors which are exercised out, or removed, from the protein precursors during protein splicing. The protein sequences flanking inteins are called exteins. The excision of an intein is associated with the concomitant ligation of the N-extein (the protein sequence to the N-terminus of the intein) and the C-extein (the protein sequence to the C-terminus of the intein) through a native peptide bond thus forming a mature extein protein and a free intein. See Perler et al., *Nucleic Acids Res.*, 22:1125–1127 (1994). The entire protein splicing process is autocatalyzed by the intein and is believed to be independent of specific host cell factors. Indeed, intein-based protein splicing has been shown to occur in vitro as well as in heterologous organisms. See Perler et al., *Cell*, 92:1–4 (1998). Intein-based protein splicing has also been shown to be independent of the native flanking exteins. Hybrid protein sequences containing inteins fused to non-native polypetide sequences are able to undergo protein splicing to excise the inteins and ligate the flanking polypeptide sequences. See e.g., Evans et al., *J. Biol. Chem.*, 274:3923–3926 (1999); Evans et al., *J. Biol. Chem.*, 275:9091–9094 (2000).

Certain amino acid sequences within an intein sequence are irrelevant to protein splicing. Based on sequence comparison and structural analysis, it is now known that the residues responsible for splicing are the intein N-terminal 100 amino acids, approximately, and the intein C-terminal 50 amino acids, approximately. See e.g., Duan et al., *Cell*, 89:555–564(1997), Hall et al., *Cell*, 91:85–97 (1997); Klabunde et al., *Nature Struct. Biol.* 5:31–36 (1998). Indeed, a functional mini-intein can be produced by deleting the centrally located irrelevant amino acid sequence leaving the N-terminal sequence of about 100 amino acids fused directly to the C-terminal sequence of about 50 amino acids. See e.g., Wu et al., *Biochim. Biophys. Acta.*, 1387:422–32 (1998). In addition, inteins have been identified that can mediate trans-splicing even when the N-terminal intein sequence and the C-terminal intein sequence are in different proteins. See id.; see also, Shingledecker et al., *Gene,* 207:187–195 (1998); Evans et al., *J. Biol. Chem.,* 274:3923–3926 (1999); Evans et al., *J. Biol. Chem.,* 275:9091–9094 (2000).

The present invention utilizes the trans-splicing capability of inteins to provide a method for detecting interactions between test agents such as proteins. Thus, in accordance with the present invention, two fusion constructs are provided: one has a first test agent and an N-intein, and the other has a second test agent and a C-intein. In addition, one or both fusion constructs have a reporter that undergoes detectable changes upon intein-mediated trans-splicing of the fusion constructs. If the first and second test agents interact with each other and bring the N-intein and C-intein into close proximity to each other, protein trans-splicing takes place. As a result, the fusion constructs are trans-spliced and/or re-ligated causing detectable changes in the reporter. By detecting the changes in the reporter, the interaction between two test agents can be determined.

As used herein, the terms "N-intein" and "C-intein" refer to an N-terminal and a C-terminal portion of an intein, respectively. An N-intein itself alone cannot direct protein splicing, and likewise, a C-intein itself alone is incapable of catalyzing protein splicing. However, when an N-intein and a C-intein are placed in close proximity, they are capable of acting in concert to catalyze protein trans-splicing. Conserved intein motifs have been identified in many inteins. Typically, an intein includes an N-terminal splicing region having sequence motifs designated A, $N_2$, B, and $N_4$, an endonuclease or linker domain region having sequence motifs designated C, D, E, and H, and a C-terminal splicing region having sequence motifs designated F and G. See Pietrokovski, *Protein Sci.,* 3:2340–2350 (1994); Pietrokovski, *Protein Sci.,* 7:64–71 (1998). Thus, in a specific embodiment, N-intein encompasses at least motifs A, $N_2$, B, and $N_4$, while C-intein includes at least motifs F and G. Typically, "N-intein" is an amino acid sequence matching the N-terminal sequence of about 90 to 110 amino acids of an intein, while "C-intein" is an amino acid sequence matching the C-terminal sequence of about 30 to 50 amino acids of an intein. A skilled artisan will recognize that optimal sequences of N-inteins and C-inteins can be determined by routine trial and error experiments. In addition, it should be understood that the terms "N-intein" and "C-intein" also encompass non-native or modified amino acid sequences that are derived from an N-terminal or C-terminal portion of an intein, respectively, e.g., modified or mutein forms containing amino acid insertions, deletions, or substitutions.

Protein precursors containing inteins have been found in all three life domains: archaea, bacteria, and eucarya. A large number of inteins exist in bacteria and yeast. See Perler et al., *Nucleic Acids Res.,* 28:1 344–5 (2000); see also *InBase, the New England Intein Database.* The N-intein and C-intein used in the fusion constructs of the present invention can be selected according to the naturally occurring intein sequences. Alternatively, the naturally occurring intein sequences can be modified by deleting, inserting, or substituting amino acids to generate desirable properties in the N- and C-intein.

Some naturally occurring native N-inteins and C-inteins are known to interact with each other. This may cause undesireable background and could yield a high frequency of false positives. To minimize the background and increase the assay sensitivity in the present invention, it is preferred to use an N-intein and a C-intein that do not substantially interact with each other. That is, they do not exhibit sufficient physical affinity to each other or form chemical bonds between them so as to bring them physically close to each other to cause substantial protein trans-splicing. Such non-interaction will be operationally defined as an inability of an N-intein/C-intein pair to yield an active reporter when fused to test agents known to have no affinity for one another.

If the N-intein and C-intein have relatively high affinity to each other, the N-intein and C-intein can be mutated to minimize their interaction. Alternatively, as will be described in detail below, competitive inhibitors of the reporters can be applied to minimize background detection signals. In this way, the detection signal from the active reporter produced by the interaction between the test proteins will be sufficiently greater than the background detection signal such that the interaction between the test proteins can be distinguished from the background interaction between the N-intein and C-intein.

Various trans-splicing assays may be used in combination with recombinant mutagenesis techniques to generate an N-intein and a C-intein that do not interact with each other and yet are capable of catalyzing protein trans-splicing when brought to proximity to each other. Conveniently, a genetic selection assay can be employed. For example, as shown in FIG. 2A, two chimeric genes can be prepared using standard recombinant DNA technologies. One chimeric gene encodes a fusion protein containing the N-terminal fragment of a reporter protein fused, at its C-terminus, to the N-terminus of an N-intein. The other chimeric gene encodes a fusion protein having a C-intein fused, at its C-terminus, to the N-terminus of the C-terminal fragment of a reporter protein. The N- and C-terminal fragments of the reporter protein should not interact with each other or with N- or C-intein. They can be in any length so long as an active reporter protein can be generated when they are ligated together through protein trans-splicing mediated by the N- and C-intein. The genetic selection assay can be performed in any suitable host cells, preferably conducted in the same type of cells in which the protein-protein interaction detection assay is conducted. The two chimeric genes are introduced to a host cell for the expression of the two fusion proteins. Alternatively, in the case of yeast cells, they can be introduced into two yeast cells having different mating types, which are subsequently mated. If the N-intein and C-intein thus expressed interact with each other, an active reporter will be detectable in the host cell. To obtain N-inteins and C-inteins that do not interact with each other, the DNA coding regions for the N-intein and C-intein are mutated using standard mutagenesis techniques to create changes in the amino acid sequences of the N- and C-intein. The thus generated mutant chimeric genes are then introduced into host cells for the genetic selection assay described above. If the active reporter is cytotoxic or cytostatic, one can select for those yeast cells that express mutant N- and C-inteins that fail to interact spontaneously. Finally, both the N- and C-extein fusion proteins can be C-terminally tagged with an epitope to allow immunologic confirmation of expression of the non-interacting intein mutants. In this manner, random mutations can be caused in the N- and C-intein and those mutant N-inteins and C-inteins that do not interact with each other are selected. See FIG. 2A.

Besides random mutagenesis, site-directed mutagenesis can also be used to change amino acid sequences in wild-type N- and C-inteins in predetermined manners. For example, amino acid sequences can be modified to create consensus sequences for phosphorylation by protein kinases or for glycosylation. Alternatively, certain amino acids in wild-type N- and C-intein sequences can also be chemically modified, e.g., by incorporating non-natural amino acids or by chemically linking certain moieties to amino acid side chains.

The selection of non-interacting N-intein and C-intein can also be done in an in vitro assay. For example, fusion proteins containing wild-type or mutated N- or C-inteins expressed from the above-described chimeric genes can be purified by standard chromatographic or affinity techniques or prepared in crude cell extracts. Fusion protein pairs (in which one contains an N-intein and the other contains a C-intein) are then mixed and incubated together in vitro under appropriate conditions to promote protein splicing as described below.

The thus selected N- and C-inteins are further tested for their ability to catalyze protein trans-splicing in a host cell. For this purpose, the selected chimeric genes containing desirable N- and C-intein coding sequences are further modified. FIG. 2B illustrates an example of this verification process. Essentially, a pair of new chimeric genes are constructed and introduced into a host cell for expressing a pair of fusion proteins. One chimeric gene encodes a fusion protein containing the above-described N-terminal fragment of a reporter protein fused, at its C-terminus, to the N-terminus of an N-intein, and a bait protein fused to the C-terminus of the N-intein. The other chimeric gene encodes a fusion protein having a C-intein fused, at its C-terminus, to the N-terminus of the above-described C-terminal fragment of a reporter protein, and a prey protein fused to the N-terminus of the C-intein. The bait protein and prey protein are known to interact with each other. Any pair of interacting proteins known in the art can be used for this purpose, such as the interacting pairs: FKBP12 and TGFβR1; FKBR12 and FRAP; thyroid hormone receptor α and nuclear corepressor 1; Ras and Raf. See Huang and Schreiber, *Proc Natl Acad Sci USA,* 94:13396–401 (1997); Rossi et al., *Proc Natl Acad Sci USA,* 94:8405–10 (1997); Chen and Evans, *Nature,* 377:454–7 (1995); Pelletier et al., *Proc Natl Acad Sci USA,* 95:12141–6 (1998) After the new chimeric genes are expressed in a host cell to produce the fusion proteins, the active reporter is detected to determine whether trans-splicing has occurred. In this manner, N-inteins and C-inteins that do not interact with each other but are nevertheless capable of mediating protein trans-splicing when they are brought into proximity can be identified.

It should be recognized that, although much of the description below is focused on protein-protein interactions, the method of the present invention for detecting interactions is applicable to any test agents, preferably macromolecules. For example, interactions among macromolecules such as oligosaccharides, lipids, nucleic acids, proteins, organic molecules including steroids and other drugs, viruses, and cells can all be detected by the present method. Thus, in accordance with present invention, two fusion constructs can be provided, one having an N-intein and a first test agent and the other having a C-intein and a second test agent. At least one of the two fusion constructs has an inactive reporter capable of being converted to an active reporter upon trans-splicing mediated by the N-intein and the C-intein. The two fusion constructs are then mixed and incubated together or allowed to contact with each other in other manners under appropriate conditions. Each of the two fusion constructs should be designed such that the interaction between the first and second test agents can be determined by detecting or measuring the active reporter in the assay system.

Optionally, a control assay is conducted in parallel to the detection assay. Typically, in the control assay, the potential interaction between the two test agents being assayed in the detection assay of this invention is pre-empted, eliminated or inhibited. For example, in one control assay, control fusion constructs are used, in which two known agents that do not interact with each other are included in lieu of the first and second test agents, respectively. Because the known agents in the control fusion constructs do not interact with each other, any active reporter signal in the control assay is a background signal. Alternatively, in another control assay, the control fusion constructs do not contain the first or second test agents. In other words, the control fusion constructs are different from those in a detection assay in that the control fusion constructs do not contain test agents. Thus, any active reporter signal in the control assay would not be the result of interaction between the test agents.

Preferably, a control assay utilizes the same two fusion constructs as those in a detection assay, which contain a first and a second test agent, respectively. However, the control assay is conducted in the presence of an inhibitor that interferes with the interaction between the first and second test agents in the fusion constructs. Typically, the inhibitor is an agent that interacts with one of the two test agents in a manner such that the interaction between the two test agents is disrupted, and as a result, the active reporter that would normally be formed upon interaction between the two test agents is not produced. Conveniently, one of the two test agents is used as an inhibitor. Such an agent should be in a free non-hybrid form or in a hybrid form that will not cause the formation of the active reporter upon an interaction between this hybrid form and the other test agent in one of the two fusion constructs. For example, if the test agent used as an inhibitor is a protein, it can be conveniently expressed from an expression vector containing a gene sequence encoding the protein.

The level of detectable active reporter in the control assay is compared to that in the detection assay. As a result, positive signals indicating specific interactions in the detection assay can be confirmed and distinguished from background signals inherent in the assay system. A control assay is especially useful when the N-intein and C-intein used in the fusion constructs can interact with each other.

A control assay can also be conducted simultaneously with the testing assay in the same host cell. In this case, the third and fourth fusion constructs described above should contain a second reporter different than that in the first and second fusion constructs such that the inability of the third and fourth fusion constructs to interact with each other can be demonstrated by detecting the presence or absence of an active form of the second reporter.

Alternatively, measures can be taken to reduce background signals. For example, in the case when cells of a His⁻ yeast strain are used as host cells and the HIS3 gene product (imidazole glycerol phosphate dehydratase) is used as a reporter, the compound 3-amino-1,2,4-triazole (3-AT) can be added to the medium on which the yeast cells in the assay are grown. 3-aminotriazole (3-AT) specifically inhibits the HIS3-encoded enzyme imidazole glycerol phosphate dehydratase which is required in yeast for the synthesis of the amino acid histidine. See Kishore et al., *Ann. Rev. Biochem.,* 57:627–663 (1988). As a result, a strong signal is required to confirm actual interaction between the test proteins. See Durfee et al., *Genes Dev.,* 7:555–569 (1993). Selection for progressively stronger reporter signaling can be achieved with progressively higher concentrations of 3-AT in the selection medium. Thus, with sufficiently high 3-AT concentrations, background growth on histidine-deficient media can be suppressed to allow use of an inherently "noisy" system.

As will be apparent to a skilled artisan, any arrangements of the components in the fusion constructs of the present invention can be adopted so long as the protein trans-splicing mediated by the N- and C-intein and initiated by a specific interaction between the test agents can be detected by measuring the active reporter produced during the protein splicing process.

Figure 3A:
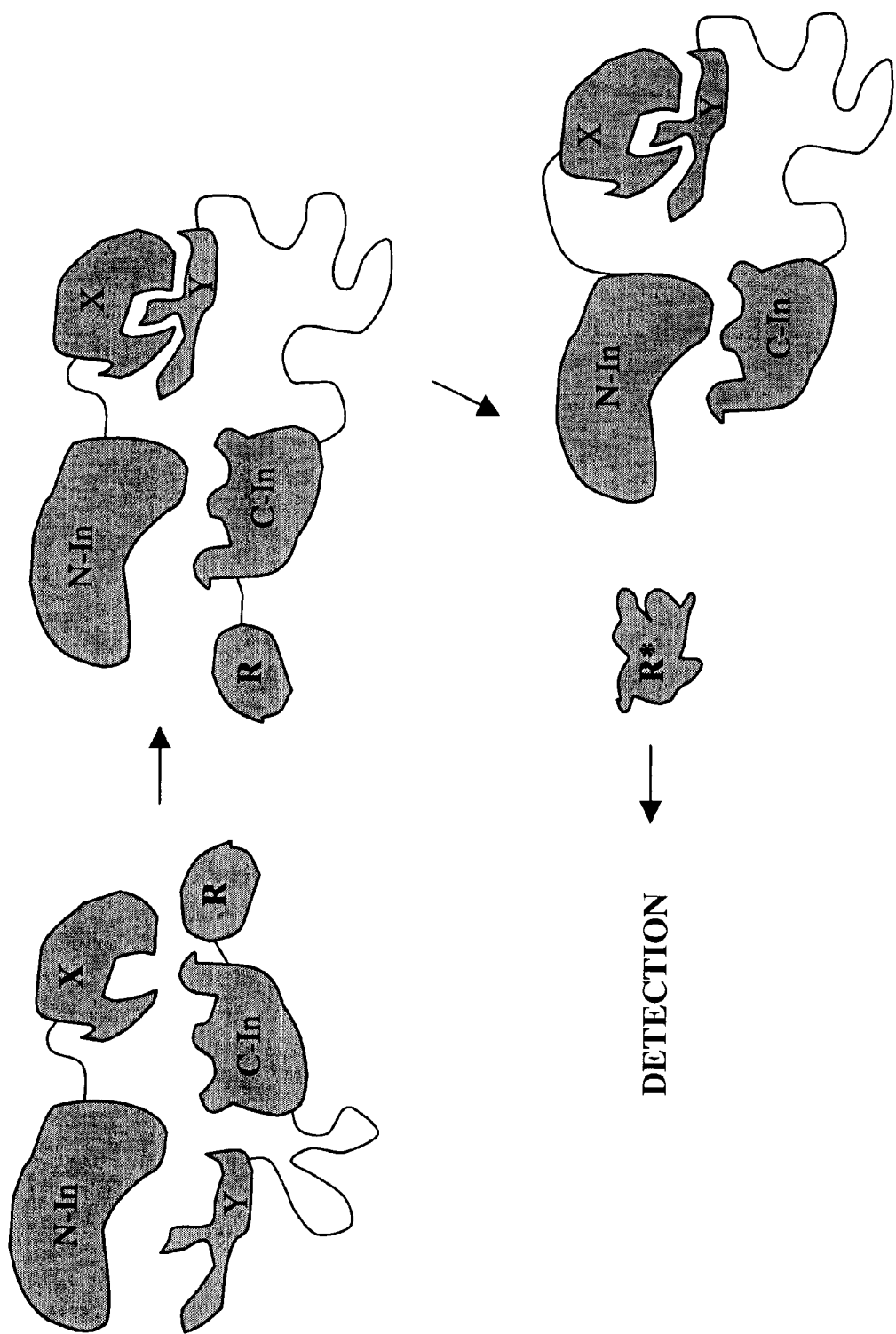
FIGS. 3A–3F are diagrams illustrating the fusion constructs in different embodiments of the present invention.

In one embodiment, as shown in FIG. 3A, one fusion construct has a first test agent X fused or conjugated to the C-terminus of an N-intein, while the other fusion construct has a second test agent Y fused to the N-terminus of a C-intein and a reporter R (inactive) fused to the C-terminus of the C-intein. Upon tans-splicing, the reporter is excised off and becomes a free detectable active reporter R*.

Figure 3B:
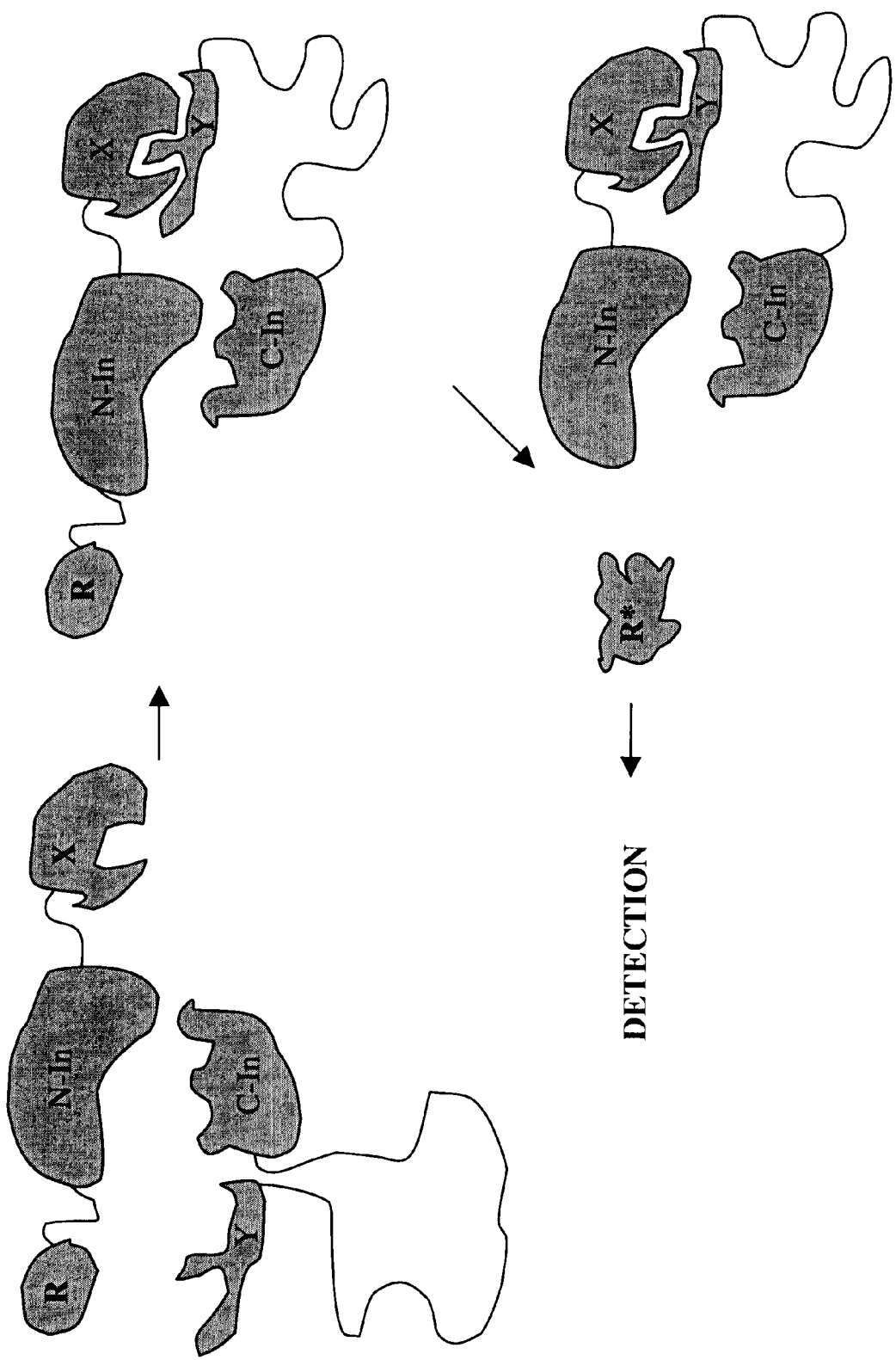

In another embodiment, as shown in FIG. 3B, one fusion construct has a first test agent X fused to the C-terminus of an N-intein and a reporter R (inactive) fused to the N-terminus of the N-intein. The other fusion construct includes a second test agent Y fused to the N-terminus of a C-intein. After trans-splicing mediated by the N- and C-intein, a detectable free active reporter R* is released.

Figure 3C:
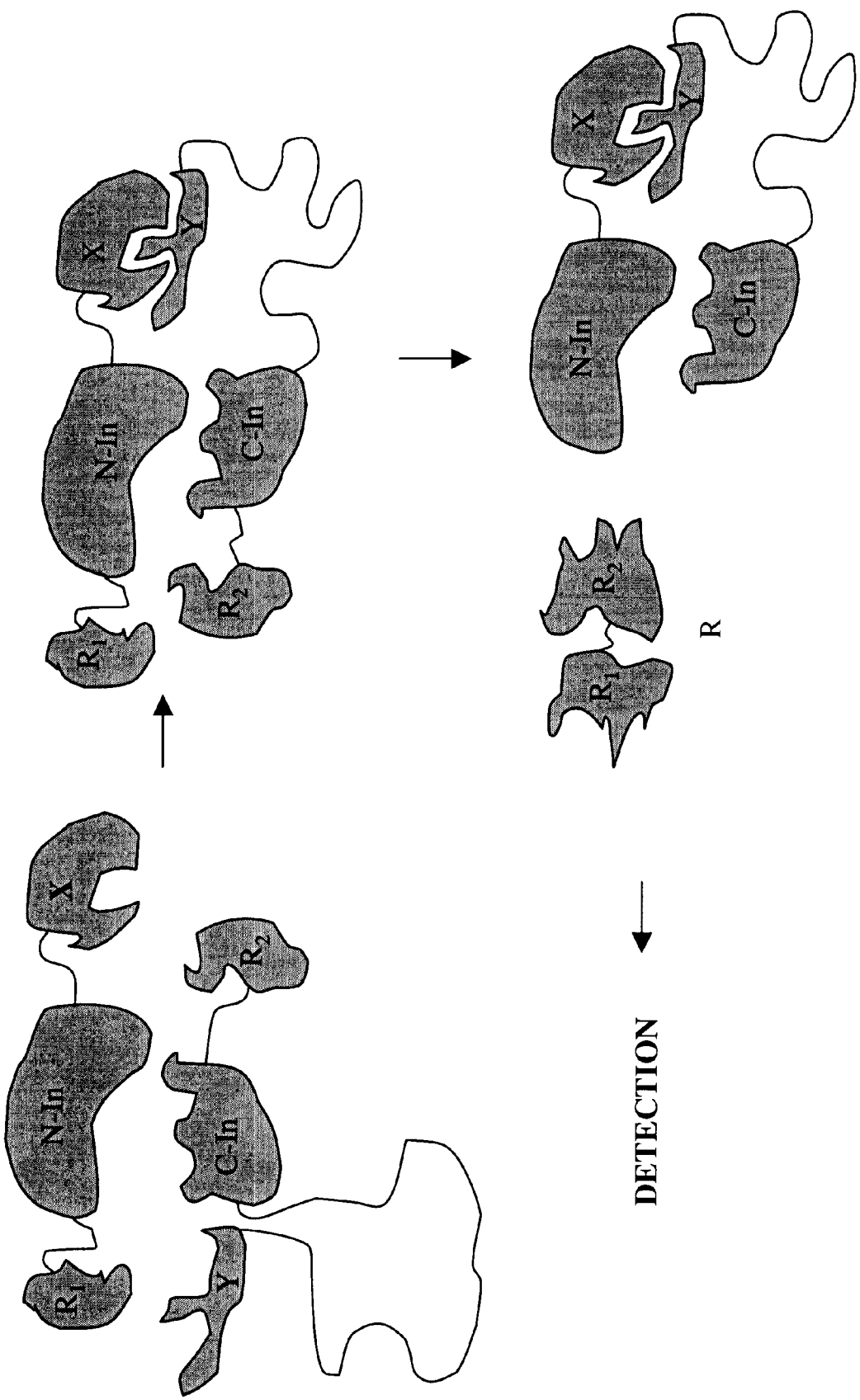

FIG. 3C illustrates the fusion construct arrangement in another embodiment of the invention. The first fusion construct consists of a first portion of a reporter R ($R_1$) fused to the N-terminus of an N-intein and a first test agent (X) fused to the C-terminus of the N-intein. The second fusion construct consists of a second test agent (Y) fused to the N-terminus of a C-intein and the remaining portion of the reporter R ($R_2$) fused to the C-terminus of the C-intein. In this manner, upon intein-directed trans-splicing, the two portions of the reporter R are ligated together thus forming a detectable active reporter R.

Figure 3D:
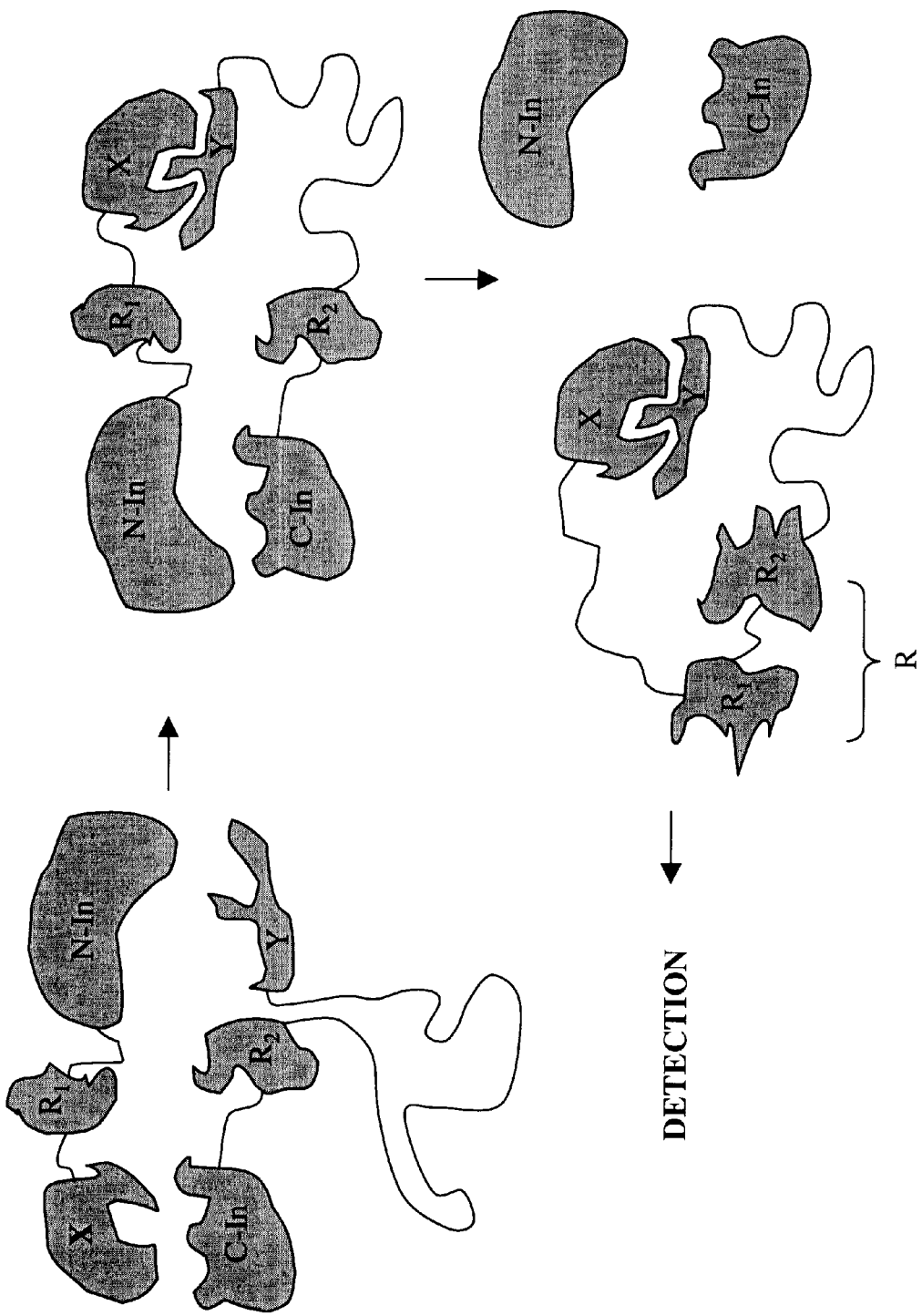

FIG. 3D is a diagram showing the fusion constructs design in yet another embodiment of the present invention. The first fusion construct consists of a first test agent (X) fused to a first portion of a reporter R ($R_1$) which in turn is fused to the N-terminus of an N-intein. The second fusion construct consists of a C-intein, the remaining portion of the reporter R ($R_2$) fused to the C-terminus of a C-intein, and a second test agent (Y) fused to $R_2$. If the test agents X and Y interact with each other to bring the N-intein and C-intein close together, trans-splicing will result in a detectable construct X-R-Y.

Figure 3E:
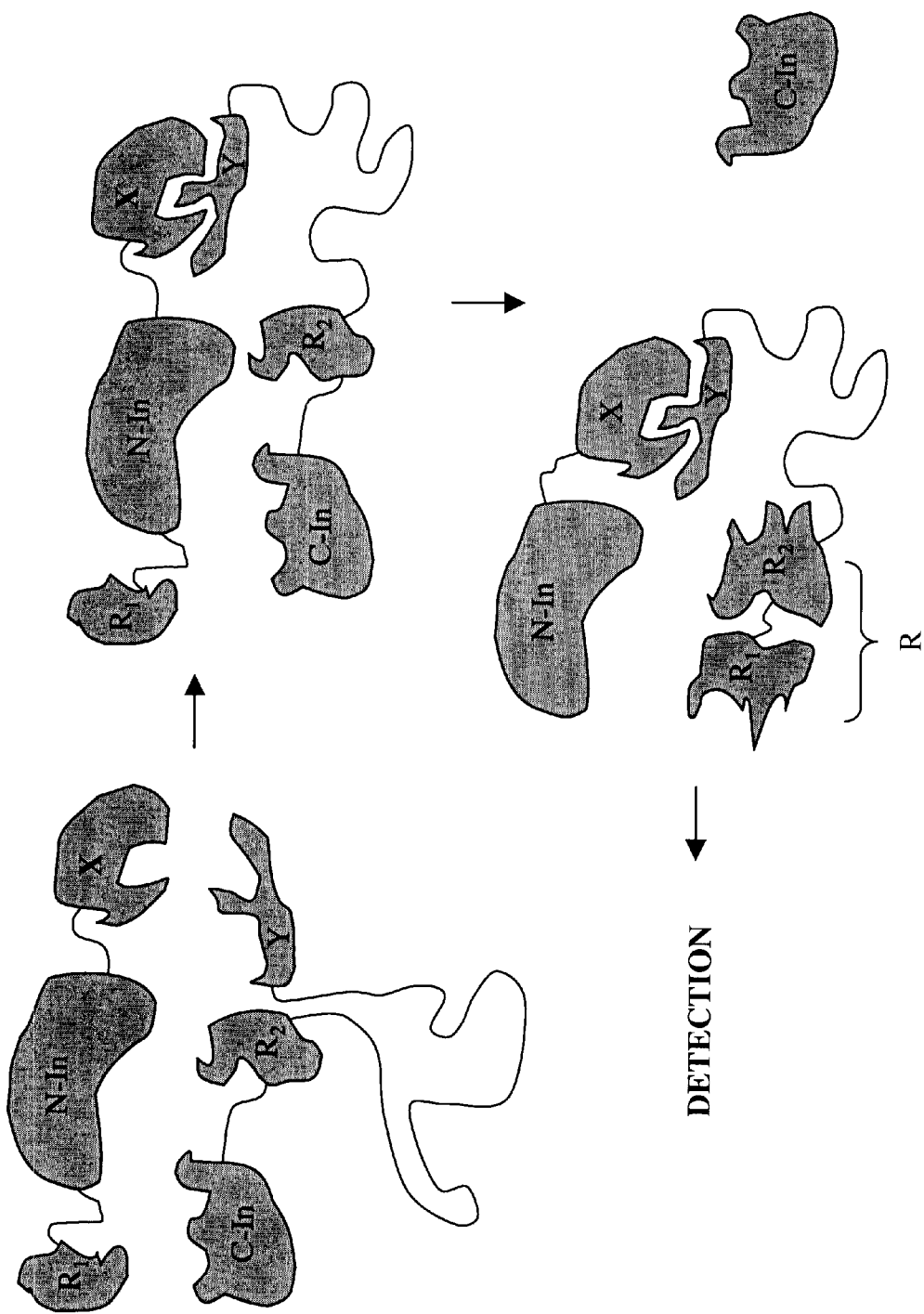

Yet another arrangement of the fusion constructs is demonstrated in FIG. 3E. The first construct is composed of a first portion of a reporter R ($R_1$) fused to the N-terminus of an N-intein and a test agent (X) fused to the C-terminus of the N-intein. The second construct has a C-intein, the remaining portion the reporter R ($R_2$) fused to the C-terminus of the C-intein, and another test agent (Y) fused to $R_2$. Assuming test agents X and Y interact with each other, thus bringing the N-intein and C-intein close together, trans-splicing can occur resulting in a detectable construct R-Y.

Figure 3F:
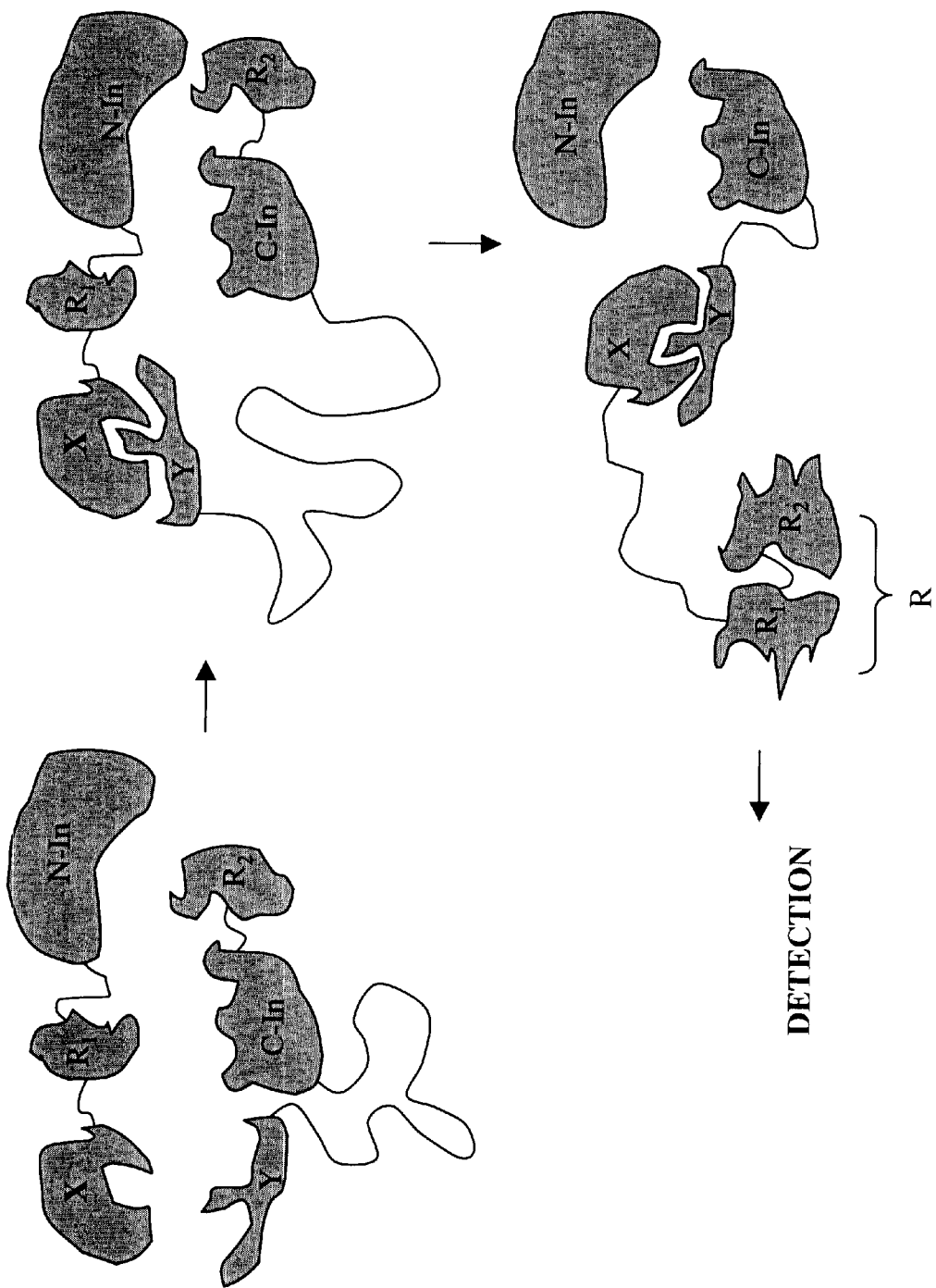

FIG. 3F illustrates yet another possible arrangement of the fusion constructs in the present invention. As shown in FIG. 3F, the first fusion construct has a test agent (X) fused to a first portion of a reporter R ($R_1$) which is in turn fused to the N-terminus of an N-intein. The second fusion construct includes another test agent (Y) fused to the N-terminus of a C-intein and the remaining portion of the reporter R ($R_2$) fused to the C-terminus of the C-intein. Assuming test agents X and Y interact with each other, thus bringing the N-intein and C-intein close together, trans-splicing can occur resulting in a detectable construct X-R.

As discussed above, the test agents can be any chemical compounds and are not limited to proteins. Likewise, both the inactive and active reporter(s) incorporated into the fusion constructs can be any suitable chemical compounds so long as specific and detectable changes can occur in the inactive reporter(s) during trans-splicing. The fusion constructs can be prepared by chemical synthesis and/or standard recombinant DNA techniques. For example, when the reporters or test agents are not protein, the N-intein and C-intein can be prepared by chemical synthesis or recombinant expression, and thereafter, the non-proteinaceous reporter or test agents can be chemically conjugated to the N-intein and/or C-intein through direct linkage or using a linker molecule. Methods for conjugating a protein or peptide to a molecule such as glycosaccharides, lipids, steroids, drugs, nucleic acids, and the like are known in the art and should be apparent to a skilled artisan apprised of the present disclosure. If both the test agents and reporters are proteins, the fusion constructs can be conveniently produced as fusion proteins by recombinantly expressing suitable chimeric genes. The fusion proteins can be extracted in a crude cell extract form or purified for in vitro assay. Purification can be achieved by conventional purification methods such as standard chromatographic or affinity techniques. Alternatively, for in vivo assays, the fusion proteins are expressed in suitable host cells and allowed to interact with each other within the host cells.

Natuarally occurring, intein-based protein splicing is largely independent of the amino acid composition of exteins with a single exception: the first residue of the C-extein is invariably cysteine, threonine, or serine. Thus, when a non-protein inactive reporter or test agent is linked to the C-terminus of the C-intein in a fusion construct of the present invention, it is preferred that the non-protein entity is conjugated to the C-intein through a linker such as amino acid cysteinene, serine, and threonine. In the case of a polypeptide reporter or polypeptide test agent fused to the C-terminus of the C-intein, it may also be preferred that the first amino acid of the polypeptide immediately following the C-terminus of the C-intein is cystenine, serine, or threonine. In the event that the C-terminus of the C-intein is exposed and not fused to any moiety, it may be desirable to design the C-intein such that it includes an additional amino acid selected from cystenine, serine, and threonine. Alternatively, a reducing thiol acid such as cysteine, mercaptoacetic acid, dithiothreitol, thiphenol, and the like may be added to the assay system. See e.g., Paulus, *Annu. Rev. Biochem.*, 69:447–496 (2000); Severinov and Muir, *J. Biol. Chem.*, 273:16205–16209 (1998). In addition, where the N-terminus of an N-intein in the fusion constructs is linked to another non-protein moiety, it is also preferable that the chemical linkage between the N-intein and the non-protein moiety is an amide linkage and preferably a peptide bond. This can be achieved by using an amino acid as a linker between the non-protein moiety to the N-terminus of the N-intein.

The detection assay in accordance with the present invention can be conducted either in vitro or in vivo in a host cell. In an in vitro assay, the fusion constructs in crude cell extracts or in purified forms can be mixed and incubated together under appropriate conditions that promote interactions between the test agents. Methods for performing in vitro trans-splicing assays are disclosed, e.g., in U.S. Pat. No. 5,834,247, which is incorporated herein by reference. It is noted that different agents may require different conditions for their interactions. As a starting point, for example, a buffer having 20 mM Tris-HCl, pH 7.0 and 500 mM NaCl may be used. Several different parameters may be varied, including temperature, pH, salt concentration, reducing agent, time, and the like. Some minor degree of experimentation may be required to determine the optimum incubation condition, this being well within the capability of one skilled in the art once apprised of the present disclosure. Cell free in vitro assays are especially suitable where the fusion constructs contain non-protein elements that cannot be synthesized by recombinant DNA technologies. In addition, in vitro assays also eliminate the constraints created by cell compartments and are useful in detecting interactions that may not be detectable in certain in vivo assays known in the art.

More conveniently, in vivo genetic assays are used in the detection method of the present invention. In this respect, fusion constructs, which normally are fusion proteins, can be recombinantly expressed in a host cell by introducing into the host cell chimeric genes encoding the fusion proteins. For this purpose, the expression vectors and host cells used in various two-hybrid systems developed in the art may be adapted and incorporated in the assays. Such two-hybrid systems are generally disclosed in U.S. Pat. Nos. 5,283,173; 5,525,490; 5,585,245; 5,637,463; 5,695,941; 5,733,726; 5,776,689; 5,885,779; 5,905,025; 6,037,136; 6,057,101; 6,114,111; and Bartel and Fields, eds., *The Yeast Two-Hybrid System*, Oxford University Press, New York, N.Y., 1997, all of which are incorporated herein by reference.

Typically, two chimeric genes are prepared encoding two fusion constructs as described above containing an N-intein and a C-intein, respectively. For the purpose of convenience, the two test polypeptides whose interaction is to be determined are referred to as "bait polypeptide" and "prey polypeptide," respectively. The chimeric genes encoding the fusion constructs containing the bait and prey polypeptides are termed "bait chimeric gene" and "prey chimeric gene," respectively. Typically, a "bait vector" and a "prey vector" are provided for the expression of a bait chimeric gene and a prey chimeric gene, respectively.

Many types of vectors can be used for the present invention. Methods for the construction of bait vectors and prey vectors should be apparent to skilled artisans in the art apprised of the present disclosure. See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516–544 (1987); *The Molecular Biology of the Yeast Saccharomyces*, Eds. Strathem et al., Cold Spring Harbor Press, Vols. I and II, 1982; and Rothstein in *DNA Cloning: A Practical Approach*, Vol. 11, Ed. D M Glover, IRL Press, Wash., D.C., 1986.

Generally, the bait and prey vectors may include a promoter operably linked to a chimeric gene for the transcription of the chimeric gene, an origin of DNA replication for the replication of the vectors in host cells and a replication origin for the amplification of the vectors in, e.g., *E. coli*, and selection marker(s) for selecting and maintaining only those host cells harboring the vectors. Additionally, the vectors preferably also contain inducible elements, which function to control the expression of the chimeric gene. Making the expression of the chimeric genes inducible and controllable is especially important in the event that the fusion proteins or components thereof are toxic to the host cells. Other regulatory sequences such as transcriptional enhancer sequences and translation regulation sequences (e.g., Shine-Dalgarno sequence) can also be included. Termination sequences such as the bovine growth hormone, SV40, lacZ and AcMNPV polyhedral polyadenylation signals may also be operably linked to the chimeric gene. An epitope tag coding sequence for detection and/or purification of the fusion proteins can also be incorporated into the expression vectors. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. Bait and prey vectors may also contain components that direct the expressed protein extracellularly or to a particular intracellular compartment. Signal peptides, nuclear localization sequences, endoplasmic reticulum retention signals, mitochondrial localization sequences, myristoylation signals, palmitoylation signals, and transmembrane sequences are example of optional vector components that can determine the destination of expressed proteins. The vectors can be introduced into the host cells by any techniques known in the art, e.g., by direct DNA transformation, microinjection, electroporation, viral infection, lipofection, gene gun, and the like. The bait and prey vectors can be maintained in host cells in an extrachromosomal state, i.e., as self-replicating plasmids or viruses. Alternatively, one or both vectors can be integrated into chromosomes of the host cells by conventional techniques such as selection of stable cell lines or site-specific recombination.

The in vivo assays of the present invention can be conducted in many different host cells, including but not limited to bacteria, yeast cells, plant cells, insect cells, and mammalian cells. A skilled artisan will recognize that the designs of the vectors can vary with the host cells used. In one embodiment, the assay is conducted in prokaryotic cells such as *Escherichia coli*, Salmonella, Klebsiella, Pseudomonas, Caulobacter, and Rhizobium. Suitable origins of replication for the expression vectors useful in this embodiment of the present invention include, e.g., the ColE1, pSC101, SV40 and M13 origins of replication. Examples of suitable promoters include, for example, the T7 promoter, the lacZ promoter, and the like. In addition, inducible promoters are also useful in modulating the expression of the chimeric genes. For example, the lac operon from bacteriophage lambda plac5 is well known in the art and is inducible by the addition of IPTG to the growth medium. Other known inducible promoters useful in a bacteria expression system include pL of bacteriophage λ, the lac promoter, the trp promoter, hybrid promoters such as the tac promoter, promoters such as the T7 promoter fused to transcriptional control elements like lacO, and the like.

In addition, selection markers sequences for selecting and maintaining only those prokaryotic cells expressing the desirable fusion proteins should also be incorporated into the expression vectors. Numerous selection markers including auxotrophic markers and antibiotic resistance markers are known in the art and can all be useful for purposes of this invention. For example, the bla gene which confers ampicillin resistance is the most commonly used selection marker in prokaryotic expression vectors. Other suitable markers include genes that confer neomycin, kanamycin, or hygromycin resistance to the host cells. In fact, many vectors are commercially available from vendors such as Invitrogen Corp. of San Diego, Calif., Clontech Corp. of Palo Alto, Calif., BRL of Bethesda, Md., and Promega Corp. of Madison, Wis. These commercially available vectors, e.g., pBR322, pSPORT, pBluescriptIISK, pcDNAI, and pcD-NAII all have a multiple cloning site into which the chimeric genes of the present invention can be conveniently inserted using conventional recombinant techniques. The constructed expression vectors can be introduced into host cells by various transformation or transfection techniques generally known in the art.

In another embodiment, mammalian cells are used as host cells for the expression of the fusion proteins and detection of protein-protein interactions. For this purpose, virtually any mammalian cell can be used including normal tissue cells, stable cell lines, and transformed tumor cells. Conveniently, mammalian cell lines such as CHO cells, Jurkat T cells, NIH 3T3 cells, HEK-293 cells, CV-1 cells, COS-1 cells, HeLa cells, VERO cells, MDCK cells, W138 cells, and the like are used. Mammalian expression vectors are well known in the art and many are commercially available. Examples of suitable promoters for the transcription of the chimeric genes in mammalian cells include viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus promoter (e.g., 7.5K promoter), and herpes simplex virus (HSV) (e.g., thymidine kinase promoter). Inducible promoters can also be used. Suitable inducible promoters include, for example, the tetracycline responsive element (TRE) (See Gossen et al., *Proc. Natl. Acad. Sci. USA*, 89:5547–5551 (1992)), metallothionein IIA promoter, ecdysone-responsive promoter, and heat shock promoters. Suitable origins of replication for the replication and maintanence of the expression vectors in mammalian cells include, e.g., the Epstein Barr origin of replication in the presence of the Epstein Barr nuclear antigen (see Sugden et al., *Mole. Cell. Biol.*, 5:410–413 (1985)) and the SV40 origin of replication in the presence of the SV40 T antigen (which is present in COS-1 and COS-7 cells) (see Margolskee et al., *Mole. Cell. Biol.*, 8:2837 (1988)). Suitable selection markers include, but are not limited to, genes conferring resistance to neomycin, hygromycin, zeocin, and the like. Many commercially available mammalian expression vectors may be useful for the present invention, including, e.g., pCEP4, pcDNAI, pIND, pSecTag2, pVAX1, pcDNA3.1, and pBI-EGFP, and pDisplay. The vectors can be introduced into mammalian cells using any known techniques such as calcium phosphate precipitation, lipofection, electroporation, and the like. The bait vector and prey vector can be co-transformed into the same cell or, alternatively, introduced into two different cells which are subsequently fused together by cell fusion or other suitable techniques.

Viral expression vectors, which permit introduction of recombinanat genes into cells by viral infection, can also be used for the expression of the fusion proteins. Typically, viral vectors having the chimeric genes incorporated therein are viable and can be easily introduced into host cells by viral infection. Viral expression vectors generally known in the art include viral vectors based on adenovirus, bovine papilloma virus, murine stem cell virus (MSCV), MFG virus, and retrovirus. See Sarver, et al., *Mol. Cell. Biol.*, 1: 486 (1981); Logan & Shenk, *Proc. Natl. Acad. Sci. USA*, 81:3655–3659 (1984); Mackett, et al., *Proc. Natl. Acad. Sci. USA*, 79:7415–7419 (1982); Mackett, et al., *J. Virol.*, 49:857–864 (1984); Panicali, et al., *Proc. Natl. Acad. Sci. USA*, 79:4927–4931 (1982); Cone & Mulligan, *Proc. Natl. Acad. Sci. USA*, 81:6349–6353 (1984); Mann et al., *Cell*, 33:153–159 (1993); Pear et al., *Proc. Natl. Acad. Sci. USA*, 90:8392–8396 (1993); Kitamura et al., *Proc. Natl. Acad. Sci. USA*, 92:9146–9150 (1995); Kinsella et al., *Human Gene Therapy*, 7:1405–1413 (1996); Hofmann et al., *Proc. Natl. Acad. Sci. USA*, 93:5185–5190 (1996); Choate et al., *Human Gene Therapy*, 7:2247 (1996); WO 94/19478; Hawley et al., *Gene Therapy*, 1:136 (1994) and Rivere et al., *Genetics*, 92:6733 (1995), all of which are incorporated by reference.

Generally, to construct a viral vector, a chimeric gene according to the present invention can be operably linked to a suitable promoter. The promoter-chimeric gene construct is then inserted into a non-essential region of the viral vector, typically a modified viral genome. This results in a viable recombinant virus capable of expressing the fusion protein encoded by the chimeric gene in infected host cells. Once in the host cell, the recombinant virus typically is integrated into the genome of the host cell. However, recombinant bovine papilloma viruses typically replicate and remain as extrachromosomal elements.

In another embodiment, the detection assays of the present invention are conducted in plant cell systems. Methods for expressing exogenous proteins in plant cells are well known in the art. See generally, Weissbach & Weissbach, *Methods for Plant Molecular Biology*, Academic Press, NY, 1988; Grierson & Corey, *Plant Molecular Biology*, 2d Ed., Blackie, London, 1988. Recombinant virus expression vectors based on, e.g., cauliflower mosaic virus (CaMV) or tobacco mosaic virus (TMV) can all be used. Alternatively, recombinant plasmid expression vectors such as Ti plasmid vectors and Ri plasmid vectors are also useful. The chimeric genes encoding the fusion proteins of the present invention can be conveniently cloned into the expression vectors and placed under control of a viral promoter such as the 35S RNA and 19S RNA promoters of CaMV or the coat protein promoter of TMV, or of a plant promoter, e.g., the promoter of the small subunit of RUBISCO and heat shock promoters (e.g., soybean hsp17.5-E or hsp17.3-B promoters).

In addition, the in vivo assay of the present invention can also be conducted in insect cells, e.g., *Spodoptera frugiperda* cells, using a baculovirus expression system. Expression vectors and host cells useful in this system are well known in the art and are generally available from various commercial vendors. For example, the chimeric genes of the present invention can be conveniently cloned into a non-essential region (e.g., the polyhedrin gene) of an *Autographa californica* nuclear polyhedrosis virus (AcNPV) vector and placed under control of an AcNPV promoter (e.g., the polyhedrin promoter). The non-occluded recombinant viruses thus generated can be used to infect host cells such as *Spodoptera frugiperda* cells in which the chimeric genes are expressed. See Smith, U.S. Pat. No. 4,215,051.

In a preferred embodiment of the present invention, the fusion proteins are expressed in a yeast expression system using yeasts such as *Saccharomyces cerevisiae, Hansenula polymorpha, Pichia pastoris,* and *Schizosaccharomyces pombe* as host cells. The expression of recombinant proteins in yeasts is a well developed area, and the techniques useful in this respect is disclosed in detail in *The Molecular Biology of the Yeast Saccharomyces*, Eds. Strathem et al., Vols. I and II, Cold Spring Harbor Press, 1982; Ausubel et al., *Current Protocols in Molecular Biology*, New York, Wiley, 1994; and Guthrie and Fink, *Guide to Yeast Genetics and Molecular Biology*, in *Methods in Enzymology*, Vol. 194, 1991, all of which are incorporated herein by reference. Sudbery, *Curr. Opin. Biotech.*, 7:517–524 (1996) reviews the success in the art in expressing recombinant proteins in various yeast species; the entire content and references cited therein are incorporated herein by reference. In addition, Bartel and Fields, eds., *The Yeast Two-Hybrid System,* Oxford University Press, New York, N.Y., 1997 contains extensive discussions of recombinant expression of fusion proteins in yeasts in connection with various yeast two-hybrid systems, and cites numerous relevant references. These and other methods known in the art can all be used for purposes of the present invention. The application of such methods to the present invention should be apparent to a skilled artisan apprised of the present disclosure.

Generally, each of the two chimeric genes (one having an N-intein coding sequence and the other having a C-intein coding sequence) of the present invention is included into a separate expression vector (bait vector and prey vector). Both vectors can be co-transformed into a single yeast host cell. As will be apparent to a skilled artisan, it is also possible to express both chimeric genes from a single vector. In a preferred embodiment, the bait vector and prey vector are introduced into two haploid yeast cells of opposite mating types, e.g., a-type and α-type, respectively. The two haploid cells can be mated at a desired time to form a diploid cell expressing both chimeric genes.

Generally, the bait and prey vectors for recombinant expression in yeasts include a yeast replication origin such as the 2μ origin or the ARSH4 sequence for the replication and maintenance of the vectors in yeast cells. Preferably, the vectors also have a bacteria origin of replication (e.g., ColE1) and a bacteria selection marker (e.g., amp$^R$ marker, i.e., bla gene). Optionally, the CEN6 centromeric sequence is included to control the replication of the vectors in yeast cells. Any constitutive or inducible promoters capable of driving gene transcription in yeast cells may be employed to control the expression of the chimeric genes. Such promoters are operably linked to the chimeric genes. Examples of suitable constitutive promoters include but are not limited to the yeast ADH1, PGK1, TEF2, GPD1, HIS3, and CYC1 promoters. Example of suitable inducible promoters include but are not limited to the yeast GAL1 (inducible by galactose), CUP1 (inducible by Cu$^{++}$), MEL1 (inducible by galactose), FUS1 (inducible by pheromone) promoters; the AOX/MOX promoter from *H. polymorpha* and *P. Pastoris* (repressed by glucose or ethanol and induced by methanol); chimeric promoters such as those that contain LexA operators (inducible by LexA-containing transcription factors); and the like. Inducible promoters are preferred when the fusion proteins encoded by the chimeric genes or the reporter proteins resulting from protein trans-splicing are toxic to the host cells. If it is desirable, certain transcription repressing sequences such as the upstream repressing sequence (URS) from SPO13 promoter can be operably linked to the promoter sequence, e.g., linked to the 5' end of the promoter region. Such upstream repressing sequences function to fine-tune the expression level of the chimeric genes.

Preferably, a transcriptional termination signal is operably linked to the chimeric genes in the vectors. Generally, transcriptional termination signal sequences derived from, e.g., the CYC1 and ADH1 genes can be used.

Additionally, it is preferred that the bait vector and prey vector contain one or more selectable markers for the selection and maintenance of only those yeast cells that harbor the chimeric genes of the present invention. Any selectable markers known in the art can be used for purposes of this invention so long as yeast cells expressing the chimeric gene(s) of the present invention can be positively identified or negatively selected. Examples of markers that can be positively identified are those based on color assays, including the lacZ gene which encodes β-galactosidase, the firefly luciferase gene, secreted alkaline phosphatase, horseradish peroxidase, the blue fluorescent protein (BFP), and the green fluorescent protein (GFP) gene (see Cubitt et al., *Trends Biochem. Sci.,* 20:448–455 (1995)). Other markers emitting fluorescence, chemiluminescence, UV absorption, infrared radiation, and the like can also be used. Among the markers that can be selected are auxotrophic markers that include, but are not limited to, URA3, HIS3, TRP1, LEU2, LYS2, ADE2, and the like. Typically, for purposes of auxotrophic selection, the yeast host cells transformed with bait vector and/or prey vector are cultured in a medium lacking a particular nutrient. Other selectable markers are not based on auxotrophies, but rather on resistance or sensitivity to an antibiotic or other xenobiotic. Examples include but are not limited to chloramphenicol acetyl transferase (CAT) gene, which confers resistance to chloramphenicol; CAN1 gene, which encodes an arginine permease and thereby renders cells sensitive to canavanine (see Sikorski et al., *Meth. Enzymol.,* 194:302–318 (1991)); the bacterial kanamycin resistance gene (kan$^R$), which renders eucaryotic cells resistant to the aminoglycoside G418 (see Wach et al., *Yeast,* 10:1793–1808 (1994)); and CYH2 gene, which confers sensitivity to cycloheximide (see Sikorski et al., *Meth. Enzymol.,* 194:302–318 (1991)). In addition, the CUP1 gene, which encodes metallothionein and thereby confers resistance to copper, is also a suitable selection marker. Each of the above selection markers may be used alone or in combination. One or more selection markers can be included in a particular bait or prey vector. The bait vector and prey vector may have the same or different selection markers. In addition, the selection pressure can be placed on the transformed host cells either before or after mating the haploid yeast cells.

As will be apparent, the selection markers used should complement the host strains in which the bait and/or prey vectors are expressed. In other words, when a gene is used as a selection marker gene, a yeast strain lacking the selection marker gene (or having mutation in the corresponding gene) should be used as host cells. Numerous yeast strains or derivative strains corresponding to various selection markers are known in the art. Many of them have been developed specifically for certain yeast two-hybrid systems. The application and optional modification of such strains with respect to the present invention should be apparent to a skilled artisan apprised of the present disclosure. Methods for genetically manipulating yeast strains using genetic crossing or recombinant mutagenesis are well known in the art. See e.g., Rothstein, *Meth. Enzymol.,* 101:202–211 (1983). By way of example, the following yeast strains are well known in the art, and can be used in the present invention upon necessary modifications and adjustment:

L40 strain which has the genotype MATa his3Δ200 trp1-901 leu2-3,112 ade2 LYS2::(lexAop)4-HIS3 URA3::(lexAop)8-lacZ;

EGY48 strain which has the genotype MATa trp1 his3 ura3 6ops-LEU2; and

MaV103 strain which has the genotype MATa ura3-52 leu2-3,112 trp1-901 his3Δ200 ade2-101 gal4Δ gal80Δ SPAL10::URA3 GAL1::HIS3::lys2 (see Kumar et al., *J. Biol. Chem.* 272:13548–13554 (1997); Vidal et al., *Proc. Natl. Acad. Sci. USA,* 93:10315–10320 (1996)). Such strains are generally available in the research community, and can also be obtained by simple yeast genetic manipulation. See, e.g., *The Yeast Two-Hybrid System,* Bartel and Fields, eds., pages 173–182, Oxford University Press, New York, N.Y., 1997.

In addition, the following yeast strains are commercially available:

Y190 strain which is available from Clontech, Palo Alto, Calif. and has the genotype MATa gal4 gal80 his3Δ200 trp1-901 ade2-101 ura3-52 leu2-3, 112 URA3::GAL1-lacZ LYS2::GAL1-HIS3 cyh$^r$; and YRG-2 Strain which is available from Stratagene, La Jolla, Calif. and has the genotype MATα ura3-52 his3-200 ade2-101 lys2-801 trp1-901 leu2-3, 112 gal4-542 gal80-538 LYS2::GAL1-HIS3 URA3::GAL1/CYC1-lacZ.

In fact, different versions of vectors and host strains specially designed for yeast two-hybrid system analysis are available in kits from commercial vendors such as Clontech, Palo Alto, Calif. and Stratagene, La Jolla, Calif., all of which can be modified for use in the present invention.

As described above, each of the two fusion constructs should be designed such that the interaction between the first and second test agents is determinable by detecting or measuring changes in the reporter in the assay system. It will be apparent from the above discussion, the reporter can be any molecules or moieties so long as changes in the reporter that are specifically associated with intein-mediated trans-splicing are detectable. It will be recognized that although the reporters and selection markers can be of similar types and used in a similar manner in the present invention, the reporters and selection markers should be carefully selected in a particular detection assay such that they are distinguishable from each other and do not interfere with each other's function.

Conveniently, the occurrence of trans-splicing can be detected by detecting changes in the size of the reporter. For example, the sizes of the various components of the fusion constructs can be designed such that the "active reporter," which is generated when the "inactive reporter" is simply cleaved off from one of the fusion constructs or recombined with one or more other components of the fusion constructs, is distinguishable from its precursor(s) and other trans-splicing products based on size, i.e., molecular weight. In both in vitro and in vivo assays, the inactive reporter can be pre-labeled with, e.g., radioactive isotope or fluorescence or other detectable markers, and the active reporter can be detected in, e.g., gel electrophoresis either before or after purification. Purification can be based on specific affinity columns using an antigen-specific protein, e.g., light-chain immunoglobulin, heavy-chain immunoglobulin, avidin, streptavidin, protein A, and antigenic peptides. Conveniently, the commonly used and commercially available epitope tags may be used as size-based reporters. Such epitope tags include sequences derived from, e.g., influenza virus hemagglutinin (HA), Simian Virus 5 (V5), polyhistidine (6xHis), c-myc, lacZ, GST, and the like. For example, proteins with polyhistidine tags can be easily detected and/or purified with Ni affinity columns. One advantage for using such epitope tags is that specific antibodies to many of these epitope tags are generally commercially available. Alternatively, an epitope-specific antibody specifically to the "active reporter" can be used to detect the level of the active reporter generated in the assay without purification.

In another embodiment, the fusion constructs are designed such that the active reporter produced during intein-mediated trans-splicing can be detected by a color-based assay. For example, when an N-terminal portion of the lacZ protein (β-galactosidase) is fused to the N-terminus of an N-intein in a fusion construct and a C-terminal portion of the lacZ protein is fused to the C-terminus of a C-intein in another fusion construct, protein trans-splicing will religate the N- and C-terminal portions of the lacZ protein to form a full-length complete and active lacZ protein. Thus, in the presence of a substrate for β-galactosidase (e.g., X-Gal, i.e., 5-bromo-4-chloro-3-indolyl-β-D-galactoside), the trans-splicing can be detected based on appearance of a blue color or by quantitative colorimetric assay. To produce the chimeric genes in this embodiment of the invention, the lacZ gene encoding β-galactosidase can be divided into a 5' portion and a 3' portion in any manner to encode an N-terminal portion and a C-terminal portion of the β-galactosidase. As discussed above, it may be advantageous to facilitate protein splicing if the first amino acid immediately following C-intein is cysteine, serine, or threonine. Thus, if at all possible, the division of the lacZ gene is made immediately before a genetic codon for cysteine, serine, or threonine such that the first amino acid in the C-terminal portion of β-galactosidase immediately following a C-intein in a fusion construct is one of the three preferred amino acids. Certain mutations may also be introduced into the lacZ gene to substitute a cysteine, serine or threonine for another amino acid, or for any other purposes, so long as the mutation does not adversely interfere with protein trans-splicing or the detection of the active reporter protein, i.e., β-galactosidase.

As will be apparent, many other reporters can be used in a similar manner in the present invention. Such other reporters include, for example, the green fluorescent protein (GFP), which can be detected by fluorescence assay and sorted by flow-activated cell sorting (FACS) (See Cubitt et al., *Trends Biochem. Sci.*, 20:448–455 (1995)), secreted alkaline phosphatase, horseradish peroxidase, the blue fluorescent protein (BFP), and luciferase photoproteins such as aequorin, obelin, mnemiopsin, and berovin (See U.S. Pat. No. 6,087,476, which is incorporated herein by reference).

Figure 4:
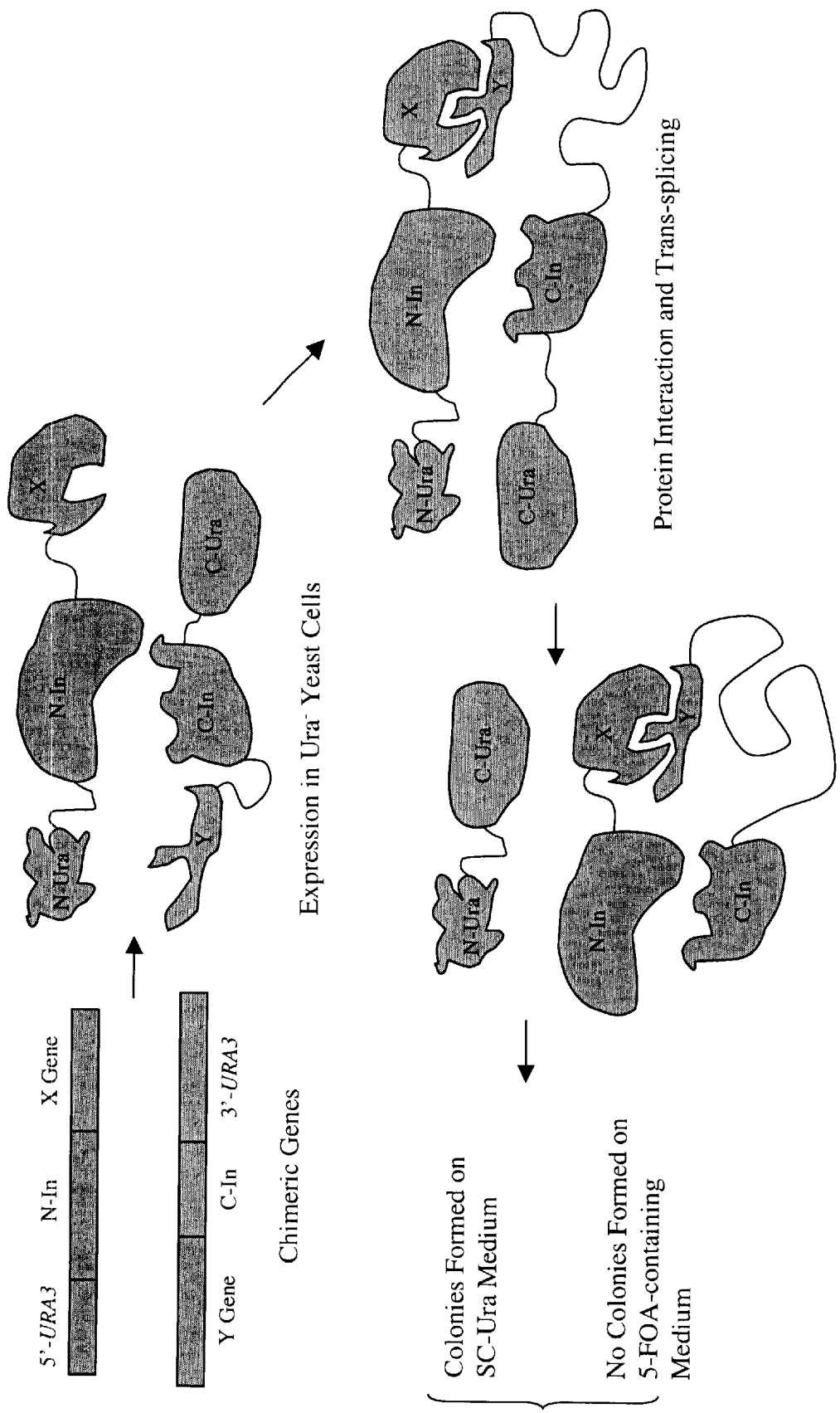
FIG. 4 is a drawing demonstrating the use of the protein encoded by the URA3 gene as a reporter protein in one embodiment of the present invention.

In another embodiment, an auxotrophic factor is used as a reporter in an in vivo assay in a host strain deficient in the auxotrophic factor. Thus, suitable auxotrophic reporter genes include, but not are limited to, URA3, HIS3, TRP1, LEU2, LYS2, ADE2, and the like. For example, yeast cells containing a mutant URA3 gene can be used as host cells (Ura$^-$ phenotype) for the in vivo assay as illustrated in FIG. 4. Such cells lack URA3-encoded functional orotidine-5'-phosphate decarboxylase, an enzyme required by yeast cells for the biosynthesis of uracil. As a result, the cells are unable to grow on a medium lacking uracil. However, wild-type orotidine-5'-phosphate decarboxylase catalyzes the conversion of a non-toxic compound 5-fluoroorotic acid (5-FOA) to a toxic product, 5-fluorouracil. Thus, yeast cells containing a wild-type URA3 gene are sensitive to 5-FOA and cannot grow on a medium containing 5-FOA. Therefore, when an N-terminal portion of the URA3-encoded protein (orotidine-5'-phosphate decarboxylase) is fused to the N-terminus of an N-intein in a fusion construct and a C-terminal portion of the URA3-encoded protein is fused to the C-terminus of a C-intein in another fusion construct, protein trans-splicing initiated by interaction between the test proteins in the fusion constructs will result in ligation of the N- and C-terminal portions of the URA3-encoded protein, thereby forming a full-length, complete, and active orotidine-5'-phosphate decarboxylase. This enables the Ura$^-$ Foa$^R$ yeast cells to grow on a uracil deficient medium (SC-Ura plates). However, such cells will not survive on a medium containing 5-FOA. Therefore, protein trans-splicing events and interactions between test proteins can be detected based on cell growth.

Additionally, antibiotic resistance reporters can also be employed in a similar manner. In this respect, host cells sensitive to a particular antibiotics is used. Antibiotics resistance reporters include, for example, chloramphenicol acetyl transferase (CAT) gene and the kan[R] gene, which confers resistance to G418 in eucaryotes and to kanamycin in prokaryotes.

Figure 5:
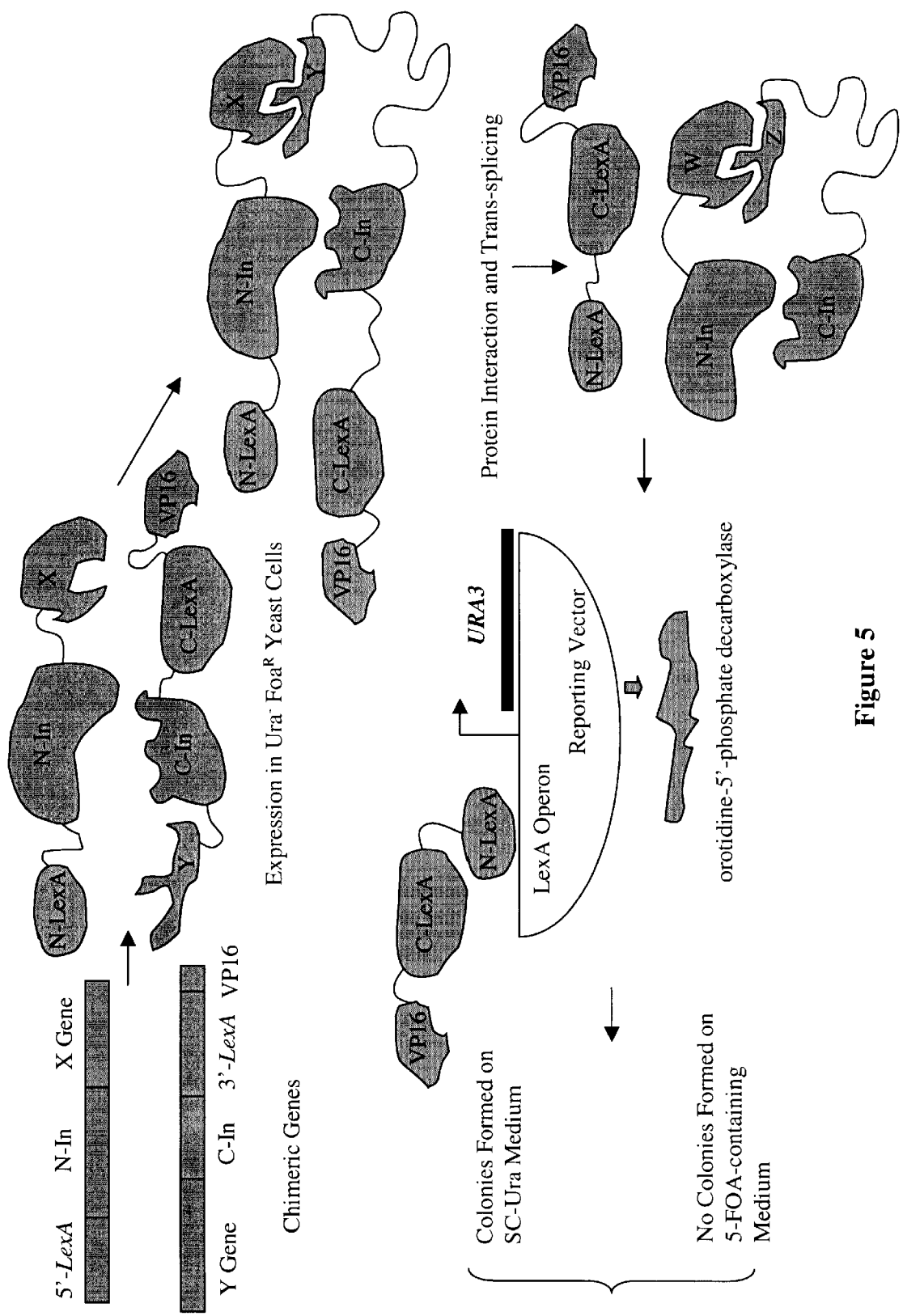
FIG. 5 shows an embodiment of the present invention in which a transcriptional activator is used as an active reporter which drives the expression of the selection marker gene URA3.

In yet another embodiment of the present invention, the fusion constructs are designed such that intein-mediated trans-splicing produces an active reporter that is a transcriptional activator or repressor capable of activating or repressing the expression of a detectable gene. Thus, the trans-splicing event will be detected based on the expression or suppression of the detectable gene. In this embodiment, a "reporting vector" containing the detectable gene operably linked to a transcriptional regulatory sequence is also introduced into the host cells. The above-described selection markers and reporter genes can all be used as the detectable gene for this purpose, so long as activation or suppression of the expression of the detectable gene is readily detectable. For example, as illustrated in FIG. 5, the URA3 gene can be used as a detectable gene in connection with either a transcriptional activator or suppressor. (An activator is shown in FIG. 5.) The URA3 gene is operably linked to a transcriptional regulatory sequence responsive to the transcriptional activator or suppressor. When the active reporter generated in trans-splicing is an activator, the yeast host cells (Ura$^-$) grow on a uracil deficient (SC-Ura) medium and the interaction between the test proteins is detected based on yeast colony formation on the medium. Alternatively, when the active reporter generated in trans-splicing is a suppressor, the yeast host cells (Ura$^-$) grow on a medium containing 5-fluoroorotic acid (5-FOA). In the absence of an interaction between the test proteins, the URA3 gene is expressed, and the 5-FOA is converted by the URA3 gene product into a toxic substance, which inhibits the growth of the host cells. In the presence of an interaction between the test proteins, a suppressor is generated and the URA3 gene expression is shut off. As a result, yeast colonies can be formed on a medium containing 5-FOA. The transcriptional regulatory sequence is designed such that the detectable gene is specifically responsive to the active reporter. Alternatively, a suitable detectable gene integrated in a chromosome of a host cell can also be used.

Suitable transcription activators include, but are not limited to, GAL4, GCN4, ARD1, the human estrogen receptor, *E. coli* LexA protein, herpes simplex virus VP16 (Triezenberg et al., *Genes Dev.* 2:718–729 (1988)), the *E. coli* B42 protein (acid blob, see Gyuris et al., *Cell,* 75:791–803 (1993)), NF-kB p65, and the like. In addition, hybrid transcriptional activators composed of a DNA binding domain from one transcriptional activator and an activation domain from another transcriptional activator are also useful. Examples of transcription suppressors include the Kruppel protein, the engrailed protein, the knirps protein, the paired protein and the even-skipped protein, all from Drosophila; the SIN3, GAL80, and TUP1 proteins, all from *Saccharomyces cerevisiae*; the tet repressor; the Egr-1, WT1, RARa, KRAB, verbA, YY1, ADE1B, E4B4, SCIP, kid-1, Znf2, and kox-1 proteins; and the like. The corresponding transcriptional elements specifically interacting with the transcriptional activators or repressors are well known in the art. See. e.g., Hanna-Rose and Hansen, *Trends. Genet.,* 12:229–234 (1996).

Thus, a transcriptional activator or repressor protein can be divided into an N-terminal portion and a C-terminal portion which are fused to the N-terminus of N-intein and C-terminus of C-intein, respectively. Upon protein transsplicing, a full-length protein emerges as a functional transcriptional activator or repressor which subsequently activates or represses the expression of the detectable gene in the reporting vector. See FIG. 5. It is recognized that the interaction between the test proteins may bring the two portions of the transcriptional activator or suppressor together which may be sufficient to initiate or suppress the transcription of the detectable gene. In this respect, this specific embodiment of the present invention may be similar to the classic yeast two-hybrid system. However, unlike the classic transcription-based yeast two-hybrid system, it is possible in the present invention to produce an active transcriptional activator or suppressor that is authentic. Thus, the fusion proteins need not be transported into cell nucleus, since the transcriptional activator or suppressor, once formed during protein trans-splicing, is competent for translocation to the nucleus. Indeed, the method of the present invention enables use of mitochondrial transcription factors as reporters. Once formed by protein trans-splicing, such reporters can translocate to the mitochondria, where they can activate or suppress transcription of mitochondrially encoded, detectable genes.

The method of the present invention for detecting protein-protein interactions can also be used to screen an expression library or applied in the so-called "interaction mating." Methods for constructing activation domain or DNA binding domain fusion libraries and the use thereof in yeast two-hybrid system are well known in the art and are disclosed in e.g., Vojtek et al., in *The Yeast Two-Hybrid System,* Bartel and Fields, eds., pages 29–42, Oxford University Press, New York, N.Y., 1997; Zhu et al., in *The Yeast Two-Hybrid System,* Bartel and Fields, eds., pages 73–96, Oxford University Press, New York, N.Y., 1997. Interaction mating is disclosed in U.S. Pat. Nos. 6,057,101 and 6,083,693; and Finley and Brent, in *The Yeast Two-Hybrid System,* Bartel and Fields, eds., pages 197–214, Oxford University Press, New York, N.Y., 1997. The methods described in the above references can all be applied to the present invention upon appropriate modifications. By way of example, N-intein fusion libraries can be prepared using an expression vector containing a 5' portion of a reporter gene operably linked to the 5' end of N-intein coding sequence. Operably linked to the 3' end of the N-intein coding sequence is a multiple cloning site into which various random or predetermined (e.g., cDNAs) DNA sequences can be inserted in frame. The DNA library thus prepared can be transformed into appropriate yeast cells. In this yeast library, an array of fusion proteins can be expressed, with each fusion protein containing an N-terminal portion of the reporter protein fused to the N-terminus of the N-intein and a random or predetermined polypeptide fused to the C-terminus of the N-intein. Appropriate yeast cells expressing a fusion protein including a bait protein fused to the N-terminus of a C-intein and the C-terminal portion of the reporter protein fused to the C-terminus of the C-intein can be used to screen the yeast N-intein fusion library to identify prey proteins capable of interacting with the bait protein.

C-intein fusion libraries can also be established and used in "interaction mating" with the N-intein fusion libraries. In this way, interacting protein pairs can be identified and genes encoding such proteins are isolated.

In yet another embodiment of the detection method of the present invention, the detection assay is used to detect interactions between three or more agents in a trimeric or higher order complex. See U.S. Pat. No. 5,695,941; Chang et al., *Cell,* 79:131–141 (1994); Tirode et al., *J. Biol. Chem.,* 272:22995–22999 (1997); Van Criekinge et al., *Anal. Biochem.,* 263:62–66 (1998); and Pause et al., *Porc. Natl. Acad. Sci. USA,* 96:9533–9538 (1999), all of which are incorporated herein by reference. Essentially, the above-described detection assay of this invention involving two fusion constructs is conducted in the presence of one or more other test agents. In this manner, interactions between the two test agents in the fusion constructs that require the participation of the other test agents can be detected.

The other test agents can be small molecule ligands that interact with the test agents in the fusion constructs. Many protein-protein interactions require the presence of a small molecule ligand, which becomes an integral part of the assembly formed by the protein interactions. See Berlin, in *The Yeast Two-Hybrid System,* Bartel and Fields, eds., pages 259–272, Oxford University Press, New York, N.Y., 1997. For example, immune suppressants such as cyclosporin A (CsA), FK506, and rapamycin are known to bind with high affinity to immunophilins forming protein-drug complexes which, in turn, bind to specific target proteins to inhibit their activities. Classic yeast two-hybrid system has been employed successfully to isolate proteins interacting with the FKBP12/rapamycin complex. See, e.g., Chiu et al., *Proc. Nat. Acad. Sci. USA,* 91:12574–12578 (1994). A multi-hybrid assay in accordance with the present invention can be conducted both in vitro and in vivo. In an in vitro assay, the small molecule ligands are simply added to the above-described intein-based two-hybrid assay system of the present invention. In an in vivo assay, it is necessary that the small molecule ligands are taken-up by the host cells. While many host cells are able to take up various small molecule ligands, certain host cells can also be manipulated to increase the uptake of small molecule ligands. For example, yeast high uptake mutants such as erg6 mutant strains can facilitate the uptake of the test compounds by yeast cells. See Gaber et al., *Mol. Cell. Biol.,* 9:3447–3456 (1989).

Many protein interactions require the participation of other proteins. Thus, the other test agents in the multi-hybrid assay of the present invention can also be proteins. Accordingly, genes encoding test proteins other than those in the intein-containing fusion constructs can be co-expressed in host cells with the chimeric genes as described above. Such additional genes may be incorporated into one of the bait or prey vector or the reporting vector. Alternatively, they can be expressed in separate vectors under control of a constitutive or inducible promoter.

Figure 6:
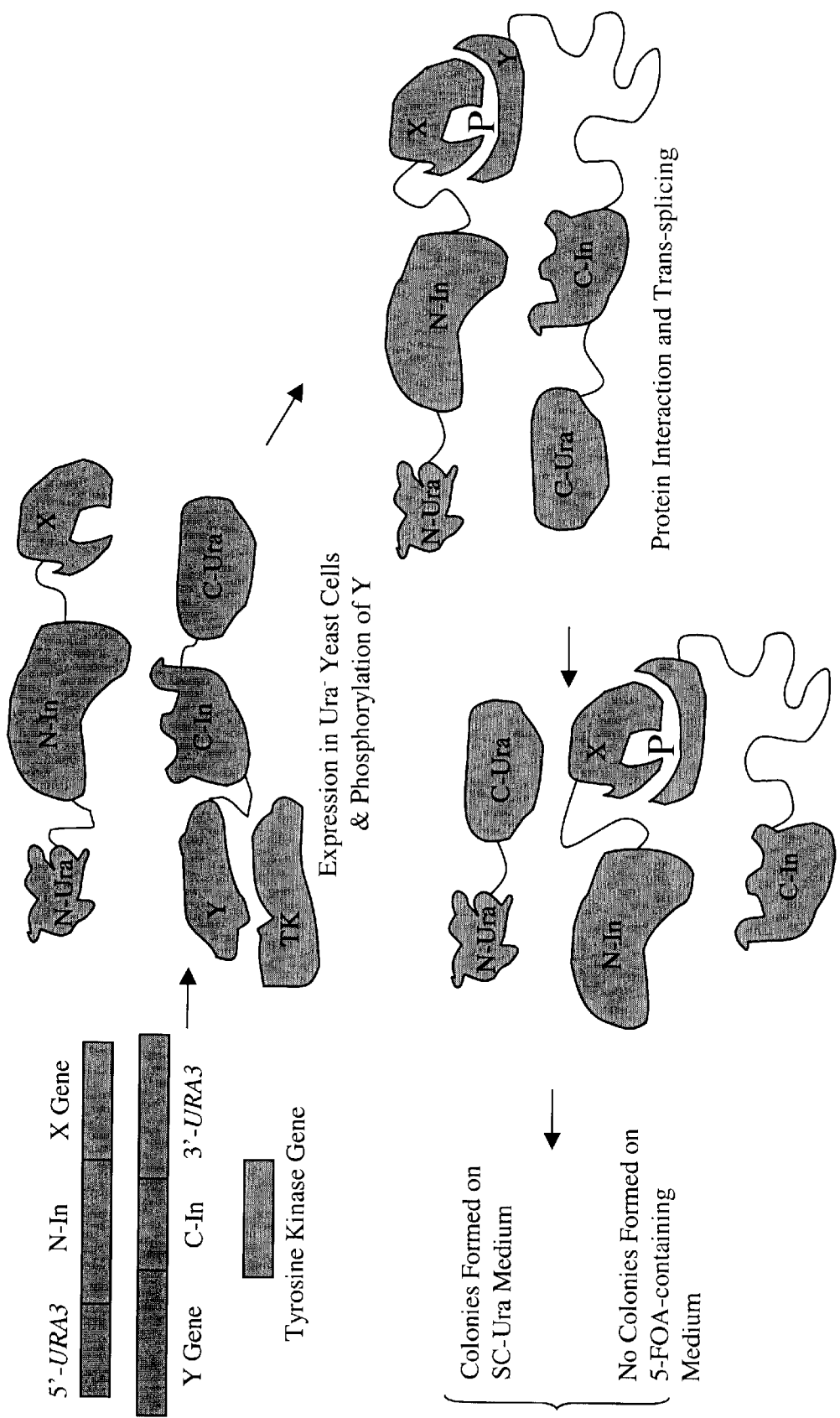
FIG. 6 is a diagram illustrating an embodiment of the present invention in which a modifying enzyme is expressed in a multi-hybrid system and interaction between the modified proteins is detected.

In a specific embodiment, the additional test proteins are enzymes capable of post-translationally modifying at least one of the test polypeptides in the intein-containing fusion constructs of the present invention. See FIG. 6. This is especially useful when one or both of the test proteins in the intein-containing fusion proteins are believed to contain consensus sequences for certain modifying enzymes. A two-hybrid system involving modifying enzymes has been disclosed in, e.g., U.S. Pat. No. 5,637,463, which is incorporated herein by reference. This system can be applied to the present invention upon appropriate modifications as will be apparent to a skilled artisan apprised of the present disclosure. Examples of useful modifying enzymes include protein kinases which catalyze protein phosphorylation (e.g., serine/threonine phosphorylation, tyrosine phosphorylation by tyrosine kinase, see Lioubin et al., *Genes Dev.,* 10:1084–1095 (1996)); Keegan et al., *Oncogene,* 12:1537–1544 (1996)), fatty acid acylation, ADP-ribosylation, myristylation, and glycosylation. In an in vivo assay, the modifying enzymes can be co-expressed in the host cells with the intein-containing fusion proteins. It is recognized that over-expression of certain modifying enzymes such as tyrosine kinases may be toxic to host cells. This can be avoided by using inducible promoters or weak promoters to drive expression of the toxic modifying enzymes in host cells.

Figure 7:
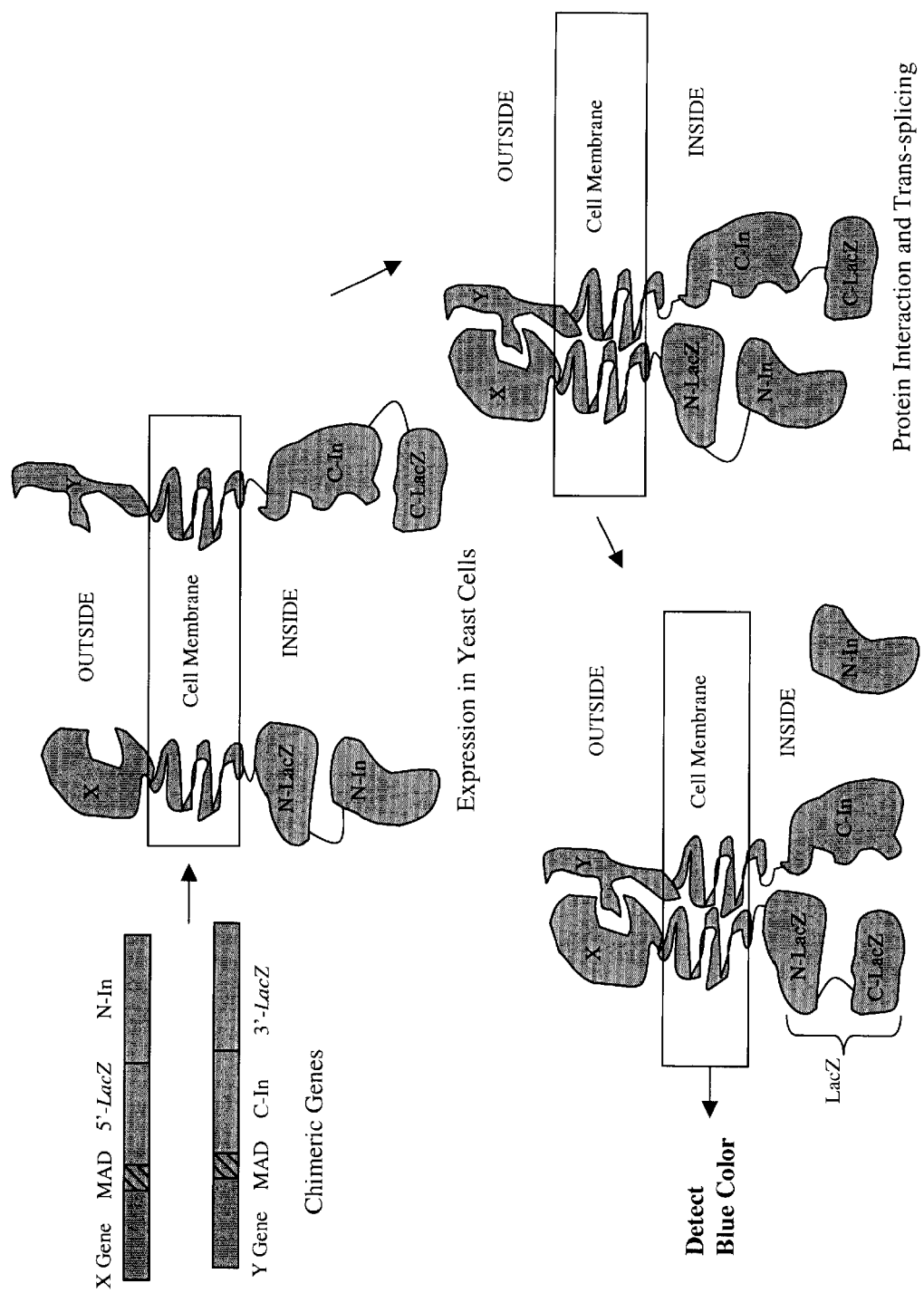
FIG. 7 is an illustration of an embodiment of the present invention in which the intein-based hybrid system is used to detect an interaction between extracellular proteins.

As discussed above, the detection method of the present invention is especially useful in detecting interactions between extracellular proteins, which has not been achieved by conventional two-hybrid systems known in the art. As shown in FIG. 7, to apply the present invention to detecting extracellular protein interactions, the intein-containing fusion proteins are designed to include a membrane anchoring domain and optionally a signal peptide such that the test proteins in the fusion proteins are exposed to extracellular environment but anchored to the cell membrane by the membrane anchoring domains. At the same time the N-intein and C-intein are retained within the host cell, so that intein-mediated protein trans-splicing can occur within the host cell and thereby generate an active reporter protein.

Many protein domains functioning to anchor proteins to cell membrane are known in the art and can all be used for purposes of the present invention. For example, the membrane anchoring domain can be a transmembrane domain derived from a known protein or an artificial sequence of hydrophobic amino acid residues sufficient to effect transmembrane spanning. Alternatively, an amino acid sequence containing a consensus sequence for post-translational modification, e.g., the covalent attachment of lipid molecules, can also be used. In addition, the membrane anchoring domain can also be a polypeptide that exhibits sufficient affinity to a cell surface protein or cell membrane component to effect binding of the molecule to the surface of the cell membrane.

Alternatively, fusion constructs can be designed to have a signal peptide or a secretion signal for protein translocation but lack a membrane anchoring domain, so that the fusion proteins are secreted into the extracellular environment to allow the detection assay to be conducted in vitro without having to purify the fusion proteins.

In accordance with another aspect of the present invention, a method is also provided for selecting a compound capable of modulating an interaction between interacting test agents including proteins. By "modulating" or "modulation" it is intended to mean that the compound interferes with, weakens, dissociates or disrupt particular protein-protein interactions, or alternatively, initiates, facilitates or stabilizes particular protein-protein interactions.

As discussed above, most proteins exercise their cellular functions through their interactions with other proteins. Protein-protein interactions form the basis of almost all biological processes. Each biological process or cell machine is composed of a network of interacting proteins. For example, many enzymatic reactions are associated with large protein complexes formed by interactions among enzymes, protein substrates and protein modulators. In addition, protein-protein interactions are also part of the mechanism for signal transduction and other basic cellular functions such as cell cycle regulation, gene transcription, and translation. Undoubtedly, protein-protein interactions are involved in various disease pathways. Thus, compounds that modulate particular protein-protein interactions in disease pathways are potential therapeutic agents useful in treating or preventing diseases. In this respect, both compounds capable of interfering with undesirable protein-protein interactions and compounds that trigger or stabilize desirable protein-protein interactions can be useful.

The intein-based system of the present invention is especially suited for screening such compounds. The screen assay in accordance with the present invention can be conducted either in vitro or in vivo using bacterial cells, yeasts, insect cells or animal cells as host cells. As will be apparent, the screen assay can be based on any of the above-described embodiments of the intein-based method for detecting protein-protein interaction. Thus, two proteins whose interaction needs to be modulated are used as test proteins in the intein-containing fusion constructs of the present invention. The two fusion constructs containing N-intein and C-intein respectively are allowed to interact with each other in the presence of a test compound, and the ability of the test compound to modulate the interaction between the two known proteins is determined by detecting the presence or absence of an active reporter or measuring the relative level of the active reporter.

The screen assay of the present invention can be used to select compounds capable of triggering or stabilizing particular protein-protein interactions. As is known in the art, many protein-protein interactions require the presence of small molecule ligands or other proteins. For example, immune suppressants such as cyclosporin A (CsA), FK506, and rapamycin are known to exert their therapeutic effect by mediating the binding of immunophilins to specific target proteins. Thus, two proteins whose interaction needs be initiated or strengthened by a therapeutic compound are used as test proteins in the intein-based two-hybrid system of the present invention. The fusion proteins are expressed and allowed to interact with each other in the presence of one or more test compounds. In an in vivo assay, e.g., in a yeast system, a positively selected marker is preferably used as a reporter. In this manner, a detectable signal (e.g., appearance of color or fluorescence, or cell survival) is present only if the test compound is able to mediate the interaction between the two test proteins.

In accordance with another aspect of the present invention, an intein-based reverse two-hybrid screen assay is provided to select compounds capable of interfering with or disrupting particular protein-protein interactions. For example, inhibitors of interactions between pathogen coat proteins and their corresponding receptors on human cell surface may be selected by the screen assay. Such inhibitors are potential preventive or therapeutic agents against the pathogen. In another example, compounds capable of dissociating interactions between oncogene products and their cellular targets are potential anti-cancer agents. Again, two proteins of interest whose interaction needs be disrupted by a therapeutic compound are used as test proteins in the intein-based two-hybrid system of the present invention. The fusion proteins are expressed and allowed to interact with each other in the presence of one or more test compounds.

In a preferred embodiment, a counterselectable marker is used as a reporter such that a detectable signal (e.g., appearance of color or fluorescence, or cell survival) is present only when the test compound is capable of interfering with the interaction between the two test proteins. In this respect, the reporters used in various "reverse two-hybrid systems" known in the art can be used. Reverse two-hybrid systems are disclosed in, e.g., U.S. Pat. Nos. 5,525,490; 5,733,726; 5,885,779; Vidal et al., *Proc. Natl. Acad. Sci. USA*, 93:10315–10320 (1996); and Vidal et al., *Proc. Natl. Acad. Sci. USA*, 93:10321–10326 (1996), all of which are incorporated herein by reference.

Examples of suitable counterselectable reporters useful in a yeast system include the URA3 gene (encoding orotidine-5'-decarboxylase, which converts 5-fluroorotic acid (5-FOA) to the toxic metabolite 5-fluorouracil), the CAN1 gene (encoding arginine permease, which transports toxic arginine analog canavanine into yeast cells), the GAL1 gene (encoding galactokinase, which catalyzes the conversion of 2-deoxygalactose to toxic 2-deoxygalactose-1-phosphate), the LYS2 gene (encoding α-aminoadipate reductase, which renders yeast cells unable to grow on a medium containing α-aminoadipate as the sole nitrogen source), the MET15 gene (encoding O-acetylhomoserine sulfhydrylase, which confers on yeast cells sensitivity to methyl mercury), and the CYH2 gene (encoding L29 ribosomal protein, which confers sensitivity to cycloheximide). In addition, any known cytotoxic agents including cytotoxic proteins such as the diphtheria toxin (DTA) catalytic domain can also be used as counterselectable reporters. See U.S. Pat. No. 5,733,726. DTA causes the ADP-ribosylation of elongation factor-2 and thus inhibits protein synthesis and causes cell death. Other examples of cytotoxic agents include ricin, Shiga toxin, and exotoxin A of *Pseudomonas aeruginosa*.

For example, when the URA3 gene is used as a counterselectable reporter gene, yeast cells containing a mutant URA3 gene can be used as host cells (Ura$^-$Foa$^R$ phenotype) for the in vivo assay. Such cells lack URA3-encoded functional orotidine-5'-phosphate decarboxylase, an enzyme required for the biosynthesis of uracil. As a result, the cells are unable to grow on media lacking uracil. However, because of the absence of a wild-type orotidine-5'-phosphate decarboxylase, the yeast cells cannot convert non-toxic 5-fluoroorotic acid (5-FOA) to a toxic product, 5-fluorouracil. Thus, such yeast cells are resistant to 5-FOA and can grow on a medium containing 5-FOA. Therefore, to screen for a compound capable of disrupting interaction between protein X and protein Y, the above-described intein-based system is utilized in which one fusion protein has an N-terminal portion of the URA3-encoded protein fused to the N-terminus of an N-intein and protein X fused to the C-terminus of the N-intein. Another fusion protein contains a C-terminal portion of the URA3-encoded protein fused to the C-terminus of a C-intein and protein Y fused to the N-terminus of the C-intein. After the fusion proteins are expressed in the Ura$^-$Foa$^R$ yeast cells, an in vivo screen assay can be conducted in the presence of a test compound with the yeast cells being cultured on a medium containing uracil and 5-FOA. If the test compound does not interrupt the interaction between protein X and protein Y, intein-mediated trans-splicing produces an active URA3 gene product, i.e., orotidine-5'-decarboxylase, which converts 5-FOA to toxic 5-fluorouracil. As a result, the yeast cells cannot grow. On the other hand, when the test compound interrupts the interaction between protein X and protein Y, intein-mediated trans-splicing does not occur and no active orotidine-5'-decarboxylase is produced in the host yeast cells. Consequently, the yeast cells will survive and grow on the 5-FOA-containing medium. Therefore, compounds capable of interfering with or dissociating particular protein-protein interactions can thus be identified based on colony formation.

As will be apparent, the screen assay of the present invention can be applied in a format appropriate for large-scale screening. For example, combinatorial technologies can be employed to construct combinatorial libraries of small organic molecules or small peptides. See generally, e.g., Kenan et al., *Trends Biochem. Sc.*, 19:57–64 (1994); Gallop et al., *J. Med. Chem.*, 37:1233–1251 (1994); Gordon et al., *J. Med. Chem.*, 37:1385–1401 (1994); Ecker et al., *Biotechnology*, 13:351–360 (1995). Such combinatorial libraries of compounds can be applied to the screen assay of the present invention to isolate specific modulators of particular protein-protein interactions. In the case of random peptide libraries, the random peptides can be co-expressed with the fusion proteins of the present invention in host cells and assayed in vivo. See e.g., Yang et al., *Nucl. Acids Res.,* 23:1152–1156 (1995). Alternatively they can be added to the host cells for uptake. Since peptides are generally not easy for cells to absorb, in vitro screen assays may be preferable. Similarly, phage display libraries can also be constructed and screened in an in vitro assay in accordance with the present invention.

Conveniently, yeast host cells are used in an in vivo screen assay. For example, haploid cells of a mating type expressing an N-intein-containing fusion protein as described above is mated with haploid cells of α mating type expressing the other fusion protein containing a C-intein. Upon mating, the diploid cells are spread on a suitable medium to form a lawn. Drops of test compounds can be deposited onto different areas of the lawn. After culturing the lawn for an appropriate period of time, drops containing a compound capable of modulating the interaction between the particular test proteins in the fusion proteins can be identified by stimulation or inhibition of growth in the vicinity of the drops.

The screen assays of the present invention for identifying compounds capable of modulating protein-protein interactions can also be fine-tuned by various techniques to adjust the thresholds or sensitivity of the positive and negative selections. For example, mutations can be introduced into the reporter proteins to adjust their activities. The uptake of test compounds by the host cells can also be adjusted. For example, yeast high uptake mutants such as the erg6 mutant strains can facilitate yeast uptake of the test compounds. See Gaber et al., *Mol. Cell. Biol.,* 9:3447–3456 (1989). Likewise, the uptake of the selection compounds such as 5-FOA, 2-deoxygalactose, cycloheximide, α-aminoadipate, and the like can also be fine-tuned.

Any test compounds may be screened in the screening assays of the present invention to select modulators of a protein-protein interaction. By the term "selecting" or "select" modulators it is intended to encompass both (a) choosing compounds from a group previously unknown to be modulators of the protein-protein interaction of interest, and (b) testing compounds that are known to be capable of modulating the protein-protein interaction of interest. Both types of compounds are generally referred to herein as "test compounds." The test compounds may include, by way of example, proteins (e.g., antibodies, small peptides, artificial or natural proteins), nucleic acids, and derivatives, mimetics and analogs thereof, and small organic molecules having a molecular weight of no greater than 10,000 daltons, more preferably less than 5,000 daltons. Preferably, the test compounds are provided in library formats known in the art, e.g., in chemically synthesized libraries, recombinantly expressed libraries (e.g., phage display libraries), and in vitro translation-based libraries (e.g., ribosome display libraries).

Peptidic test compounds may be peptides having L-amino acids and/or D-amino acids, phosphopeptides, and other types of peptides. The screened peptides can be of any size, but preferably have less than about 50 amino acids. Smaller peptides are easier to deliver into a patient's body. Various forms of modified peptides may also be screened. Like antibodies, peptides can also be provided in, e.g., combinatorial libraries. See generally, Gallop et al., *J. Med. Chem.,* 37:1233–1251 (1994). Methods for making random peptide libraries are disclosed in, e.g., Devlin et al., *Science,* 249:404–406 (1990). Other suitable methods for constructing peptide libraries and screening peptides therefrom are disclosed in, e.g., Scott and Smith, *Science,* 249:386–390 (1990); Moran et al., *J. Am. Chem. Soc.,* 117:10787–10788 (1995) (a library of electronically tagged synthetic peptides); Stachelhaus et al., *Science,* 269:69–72 (1995); U.S. Pat. Nos. 6,156,511; 6,107,059; 6,015,561; 5,750,344; 5,834,318; 5,750,344, all of which are incorporated herein by reference. For example, random-sequence peptide phage display libraries may be generated by cloning synthetic oligonucleotides into the gene III or gene VIII of an *E. coli.* filamentous phage. The thus generated phage can propagate in *E. coli.* and express peptides encoded by the oligonucleotides as fusion proteins on the surface of the phage. Scott and Smith, *Science,* 249:368–390 (1990). Alternatively, the "peptides on plasmids" method may also be used to form peptide libraries. In this method, random peptides may be fused to the C-terminus of the *E. coli.* Lac repressor by recombinant technologies and expressed from a plasmid that also contains Lac repressor-binding sites. As a result, the peptide fusions bind to the same plasmid that encodes them.

Small organic or inorganic non-peptide non-nucleotide compounds are preferred test compounds for the screening assays of the present invention. They too can be provided in a library format. See generally, Gordan et al. *J. Med. Chem.,* 37:1385–1401 (1994). For example, benzodiazepine libraries are provided in Bunin and Ellman, *J. Am. Chem. Soc.,* 114:10997–10998 (1992), which is incorporated herein by reference. A method for constructing and screening peptoid libraries are disclosed in Simon et al., *Proc. Natl. Acad. Sci. USA,* 89:9367–9371 (1992). Methods for the biosynthesis of novel polyketides in a library format are described in McDaniel et al, *Science,* 262:1546–1550 (1993) and Kao et al., *Science,* 265:509–512 (1994). Various libraries of small organic molecules and methods of construction thereof are disclosed in U.S. Pat. No. 6,162,926 (multiply-substituted fullerene derivatives); U.S. Pat. No. 6,093,798 (hydroxamic acid derivatives); U.S. Pat. No. 5,962,337 (combinatorial 1,4-benzodiazepin-2,5-dione library); U.S. Pat. No. 5,877,278 (Synthesis of N-substituted oligomers); U.S. Pat. No. 5,866,341 (compositions and methods for screening drug libraries); U.S. Pat. No. 5,792,821 (polymerizable cyclodextrin derivatives); U.S. Pat. No. 5,766,963 (hydroxypropylamine library); and U.S. Pat. No. 5,698,685 (morpholino-subunit combinatorial library), all of which are incorporated herein by reference.

Other compounds such as oligonucleotides and peptide nucleic acids (PNA), and analogs and derivatives thereof may also be screened to identify clinically useful compounds. Combinatorial libraries of oligonucleotides are also known in the art. See Gold et al., *J. Biol. Chem.,* 270:13581–13584 (1995).

Once an effective compound is identified, structural analogs or mimetics thereof can be produced based on rational drug design with the aim of improving drug efficacy and stability, and reducing side effects. Methods known in the art for rational drug design can be used in the present invention. See, e.g., Hodgson et al., *Bio/Technology,* 9:19–21 (1991); U.S. Pat. Nos. 5,800,998 and 5,891,628, all of which are incorporated herein by reference. An example of rational drug design is the development of HIV protease inhibitors. See Erickson et al., *Science,* 249:527–533 (1990).

Preferably, structural information on the protein-protein interaction to be modulated is obtained. For example, each of the interacting pair can be expressed and purified. The purified interacting protein pairs are then allowed to interact with each other in vitro under appropriate conditions. Optionally, the interacting protein complex can be stabilized by crosslinking or other techniques. The interacting complex can be studied using various biophysics techniques including, e.g., X-ray crystallography, NMR, computer modeling, mass spectrometry, and the like. Likewise, structural information can also be obtained from protein complexes formed by interacting proteins and a compound that initiates or stabilizes the interaction of the proteins.

In addition, understanding of the interaction between the proteins of interest in the presence or absence of a modulating compound can also be derived from mutagenesis analysis using the above-described detection method of the present invention. Indeed, the detection method of this invention is particularly useful in analyzing and characterizing protein-protein interactions. In this respect, various mutations can be introduced into the interacting proteins and the effect of the mutations on protein-protein interaction is examined by the above-discussed detection method.

Various mutations including amino acid substitutions, deletions and insertions can be introduced into a protein sequence using conventional recombinant DNA technologies. Generally, it is particularly desirable to decipher the protein binding sites. Thus, it is important that the mutations introduced only affect protein-protein interaction and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein-protein interactions. Alternatively, the "alanine scanning mutagenesis" technique is used. See Wells, et al., *Methods Enzymol.*, 202:301–306 (1991); Bass et al., *Proc. Natl. Acad. Sci. USA*, 88:4498–4502 (1991); Bennet et al., *J. Biol. Chem.*, 266:5191–5201 (1991); Diamond et al., *J. Virol.*, 68:863–876 (1994). Using this technique, charged or hydrophobic amino acid residues of the interacting proteins are replaced by alanine, and the effect on the interaction between the proteins is analyzed using the above-described detection method. For example, the entire protein sequence can be scanned in a window of five amino acids. When two or more charged or hydrophobic amino acids appear in a window, the charged or hydrophobic amino acids are changed to alanine using standard recombinant DNA techniques. The thus mutated proteins are used as "test proteins" in the above-described detection method to examine the effect of the mutations on protein-protein interaction. Preferably, the mutagenesis analysis is conducted both in the presence and in the absence of an identified modulating compound. In this manner, the domains or residues of the proteins important to protein-protein interaction and/or the interaction between the modulating compound and the proteins can be identified.

Based on the structural information obtained, structural relationships between the interacting proteins as well as between the identified compound and the interacting proteins are elucidated. The moieties and the three-dimensional structure of the identified compound, i.e., lead compound, critical to its modulating effect on the interaction of the known proteins of interest are revealed. Medicinal chemists can then design analog compounds having similar moieties and structures.

In addition, an identified peptide compound capable of modulating particular protein-protein interactions can also be analyzed by the alanine scanning technique to determine the domains or residues of the peptide important to its modulating effect on particular protein-protein interactions. The peptide compound can be used as a lead molecule for rational design of small organic molecules. See Huber et al., *Curr. Med. Chem.*, 1:13–34 (1994).

The residues or domains critical to the modulating effect of the identified compound constitute the active region of the compound known as its "pharmacophore." Once the pharmacophore has been elucidated, a structural model can be established by a modeling process that may incorporate data from NMR analysis, X-ray diffraction data, alanine scanning, spectroscopic techniques and the like. Various techniques including computational analysis, similarity mapping and the like can all be used in this modeling process. See e.g., Perry et al., in *QSAR: Quantitative Structure-Activity Relationships in Drug Design*, pp.189–193, Alan R. Liss, Inc., 1989; Rotivinen et al., *Acta Pharmaceutical Fennica*, 97:159–166 (1988); Lewis et al., *Proc. R. Soc. Lond.*, 236:125–140 (1989); McKinaly et al., *Annu. Rev. Pharmacol. Toxiciol.*, 29:111–122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed. The compounds identified in accordance with the present invention can be incorporated into a pharmaceutical formulation suitable for administration to an individual.

In yet another aspect of the present invention, a kit is provided comprising various vectors and reagents described above. The kit will provide users some convenience in practicing the various embodiments of the present invention. In particular, the kit can be used in detecting and/or characterizing protein-protein interactions, and in screen assays for identifying specific compounds capable of modulating known protein-protein interactions. Accordingly, components that can be included in the kit will be apparent to a skilled artisan apprised of the present disclosure. Specifically, any vectors, reagents, and the like described above in connection with various embodiments of the present invention can be included in the kit. Typically, the various components of the kit are placed in a rack, compartmentalized support or enclosed container for purposes of organizing and/or transporting the kit.

In a specific embodiment, the kit includes at least a pair of expression vectors. One expression vector contains a chimeric gene operably linked to a transcription regulatory sequence. The chimeric gene includes a DNA sequence encoding an N-intein and a multiple cloning site (MCS). The multiple cloning site is operably linked to the N-intein coding sequence such that a DNA sequence encoding a test polypeptide of interest can be conveniently inserted in frame into the MCS and a fusion protein can be produced containing the N-intein and the test polypeptide. Likewise, the other expression vector also contains a transcription regulatory sequence operably linked to a chimeric gene which includes a DNA sequence encoding a C-intein and a multiple cloning site (MCS). The multiple cloning site is operably linked to the C-intein coding sequence such that a DNA sequence encoding another test polypeptide of interest can be conveniently inserted in frame into the MCS and a fusion protein can be produced containing the C-intein and the test polypeptide. One or both of the chimeric genes further contain an operably linked DNA sequence encoding an inactive reporter protein capable of being converted to an active reporter protein upon trans-splicing mediated by the N-intein and the C-intein. Various arrangements of the chimeric genes can be used, as will apparent from the discussions above in connection with the method for detecting protein-protein interactions of the present invention. In a preferred embodiment, specially selected and/or modified coding sequences for the N-intein and C-intein are used such that the N-intein and C-intein do not significantly interact with one another.

Optionally, the chimeric genes also have DNA sequences encoding membrane anchoring domains and/or signal peptides. Such a kit will be useful in detecting or characterizing interactions between membrane or extracellular proteins, or in screen assays for identifying compounds modulating interactions between membrane or extracellular proteins.

The expression vectors may also include other components as described above in connection with the bait vectors and prey vectors of the present invention. For example, the expression vectors may contain elements necessary for the replication of the vector in a host cell, the correct transcription and translation of the chimeric gene (e.g., promoters and other transcriptional regulatory elements, transcription termination signal, etc.). The vectors preferably also contain a selection marker gene for selecting and maintaining only those host cells harboring the vectors.

For application in an intein-based multi-hybrid system of the present invention, the kit may further include one or more additional expression vectors each containing a gene encoding a test protein, e.g., a modifying enzyme (e.g., protein kinase, enzymes catalyzing glycosylation, ribosylation, myristalization, etc.). The gene may be placed under control of a constitutive or inducible promoter.

When the reporter protein is a transcription activator or suppressor, the kit may further comprise a reporting vector. As described above, the reporting vector contains a detectable gene under control of a promoter specifically activated or repressed by the activator or suppressor, respectively.

In addition, the kit of the present invention can also comprise one or more types of host cells, for example, yeast host strains for the expression of the chimeric genes and other genes. Preferably, yeast strains of opposite yeast mating types (a and α) are provided. The yeast strains should have genotypes suitable for the selection of the various vectors based on the selection marker genes in the vectors, and suitable for the detection of the active reporter generated in the host strains as a result of intein-mediated protein trans-splicing. Optionally, E. coli strains for the amplification of the various vectors are also provided in the kit.

Additionally, the kit may include instructions for using the kit to practice the present invention. The instructions should be in writing in a tangible form or stored as an electronically retrievable form.

As is apparent from the above description, the present invention provides a powerful, versatile, intein-based system for detecting and characterizing protein-protein interactions, and for selecting compounds capable of modulating protein-protein interactions. The system can be used both in vivo and in vitro with great convenience and can be easily adapted to high-throughput screening procedures. In particular, sensitive genetic selection assays can be conveniently incorporated into the system using host cells such as yeasts, bacteria, and animal cells. Detection of protein-protein interaction is based on intein-mediated protein trans-splicing, which is independent of other cellular factors. As a result, the system is useful in detecting protein-protein interactions in any intracellular compartment or even extracellularly. For example, interactions between two nuclear proteins, between between a cytosolic and a membrane-bound protein, between two mitochondrial proteins, between an extracellular and a membrane-bound protein, or between two extracellular proteins can be detected. In addition, protein trans-splicing typically results in changes in protein structures and functions and formation of free new proteins. As a result, various methods available in the art for detecting changes in protein structures and functions can be incorporated into the system allowing great flexibility in fine tuning and optimizing the system, and adapting the system to various applications.

The present invention will be further described by way of the following examples, which are not intended to limit the invention in any manner. Standard techniques well known in the art or the techniques specifically described below were utilized.

EXAMPLE

Figure 8:
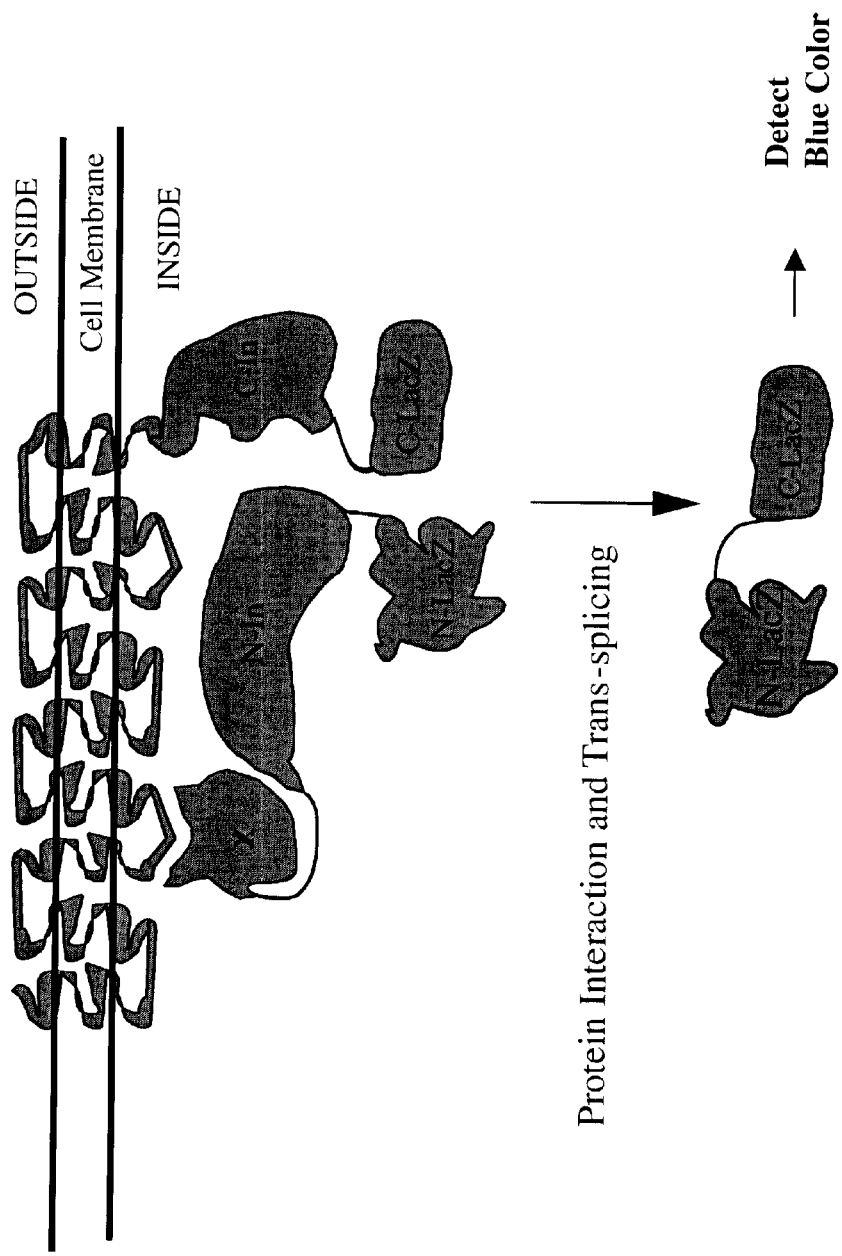
FIG. 8 illustrates an embodiment of the present invention in which the intein-based hybrid system is used to detect an interaction between an intracellular portion of a membrane protein and a cytosolic protein.

To test an intein-based two hybrid strategy, we constructed 4 vectors that allow expression of different fusion proteins (see FIG. 8):

1. Mp779. Heterologous sequences can be cloned into a polylinker that permits expression of heterologous protein fragments as a C-terminal fusion to Ura3p and intein fragments. Specifically, the fusion protein encoded by an Mp779-based expression plasmid (designated Mp779-X) will consist of the following fragments, listed from the amino to the carboxy terminus:
   residues 1 to 195 of Ura3p;
   residues 283 to 557 of the VMA1 primary translation product;
   heterologous residues (designated X) of one of two interacting proteins.

2. Mp783. Heterologous sequences can be cloned into a polylinker that permits expression of heterologous protein fragments as an N-terminal fusion to intein and Ura3p fragments. Specifically, the fusion protein encoded by an Mp783-based expression plasmid (designated Mp783-Y) will consist of the following fragments, listed from the amino to the carboxy terminus:
   heterologous protein fragment (designated Y) that interacts with X;
   residues 559 to 738 of the VMA1 primary translation product;
   residues 196 to 267 (the genuine C-terminus) of Ura3p 3. Mp778. Heterologous sequences can be cloned into a polylinker that permits expression of heterologous protein fragments as a C-terminal fusion to Ura3p and intein fragments. Specifically, the fusion protein encoded by an Mp778-based expression plasmid (designated Mp778-X) will consist of the following fragments, listed from the amino to the carboxy terminus:

residues 1 to 189 of Ura3p;

residues 283 to 557 of the VMA1 primary translation product;

heterologous residues (designated X).

4. Mp782. Heterologous sequences can be cloned into a polylinker that permits expression of heterologous protein fragments as an N-terminal fusion to intein and Ura3p fragments. Specifically, the fusion protein encoded by an Mp782-based expression plasmid (designated Mp782-Y) will consist of the following fragments, listed from the amino to the carboxy terminus:

heterologous protein fragment (designated Y) that interacts with X;

residues 559 to 738 of the VMA1 primary translation product;

residues 196 to 267 (the genuine C-terminus) of Ura3p

Using these vectors and the human genes encoding the interacting proteins BclX and Bad, we constructed the following expression plasmids:

1. Mp778-BclX
2. Mp778-Bad
3. Mp782-BclX
4. Mp782-Bad
5. Mp779-BclX
6. Mp779-Bad
7. Mp783-BclX
8. Mp783-Bad.

Figure 9:
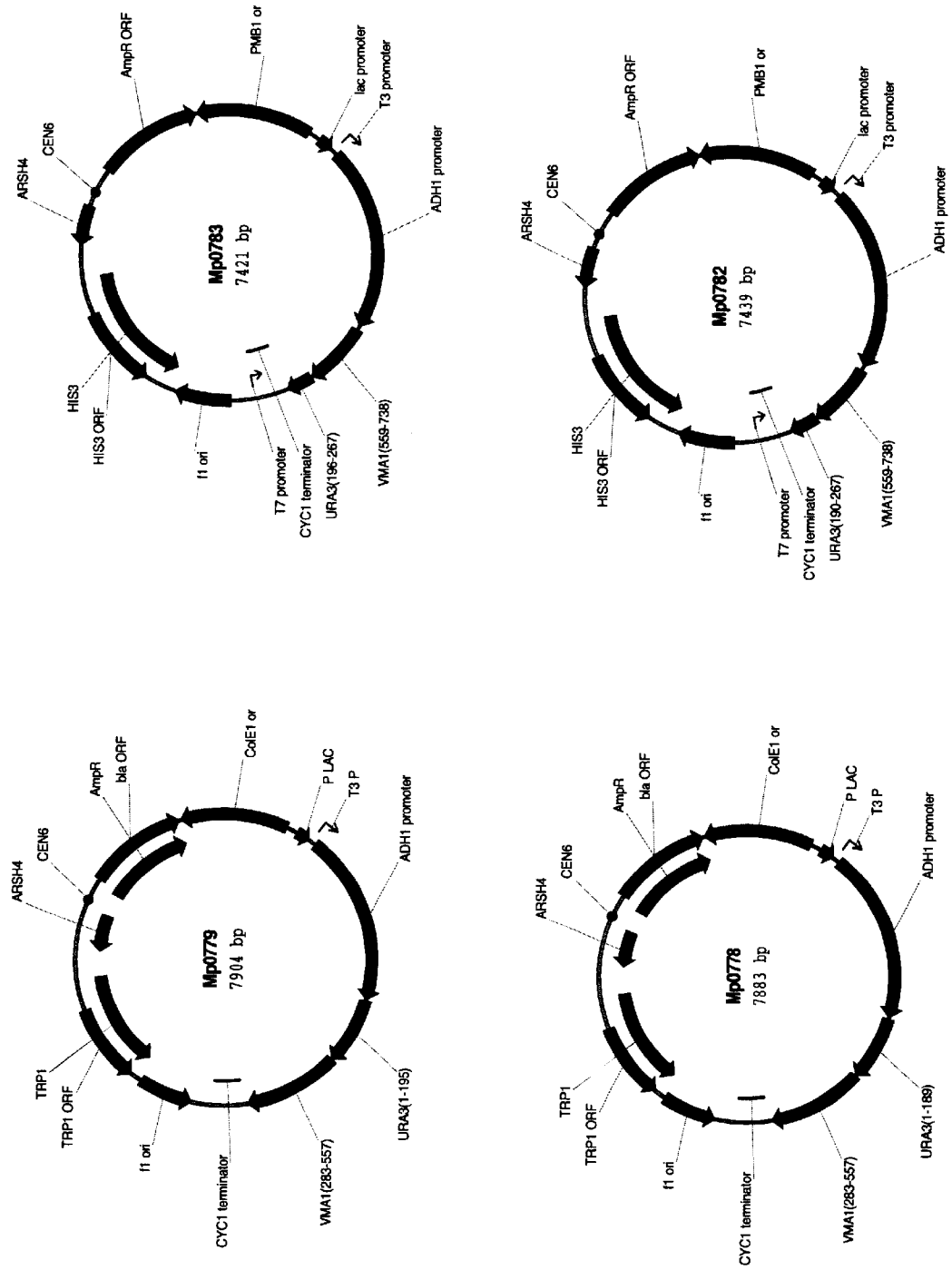
FIG. 9 illustrates four different vector constructs that allow expression of different fusion proteins used in the intein-based two-hybrid systems demonstrated in the Example.
Figure 11:
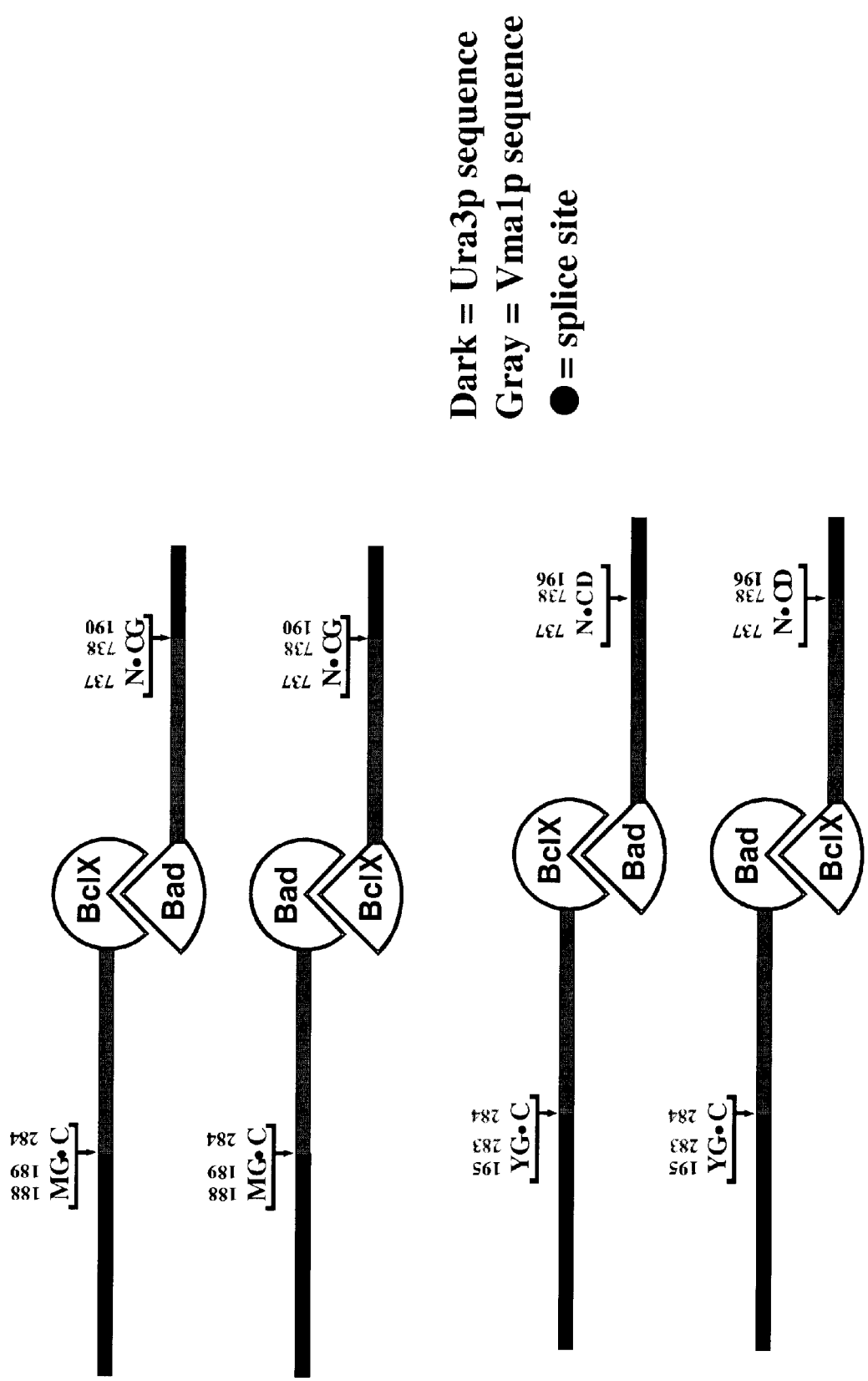
FIG. 11 illustrates the protein-protein interactions that give rise to functional Ura3p in the intein-based two-hybrid systems demonstrated in the Example.

Yeast (genotype: his3Δ200 leu2Δ0 met15Δ0 trp1Δ63 ura3Δ0) were transformed with combinations of these expression plasmids and their parental vectors to test for reconstitution of Ura3p activity that was dependent on BclX-Bad association. Two independent clones from each transformation were streaked onto media selective for Ura3p activity (SC-His-Trp-Ura) or selective only for the presence of the plasmids (SC-His-Trp). As shown in FIG. 9, yeast transformed with pairs of plasmids encoding fusion proteins that could, presumably via protein splicing, reconstitute full length Ura3p exhibited uracil prototrophy. Specifically, yeast co-transformed with the following plasmids could grow on uracil-deficient media:

Mp778-BclX and Mp782-Bad

Mp778-Bad and Mp782-BclX

Mp779-BclX and Mp783-Bad

Mp779-Bad and Mp783-BclX

A cartoon of the protein-protein interactions that are presumed to give rise to functional Ura3p is shown in FIG. 10. Notably, the uracil prototrophy was independent of "orientation" of the two-hybrid interaction; that is, it was seen whether BclX was fused to the N-terminal intein fragment and Bad was fused to the C-terminal intein fragment or vice versa. No growth was observed when strains lacked either the BclX- or Bad-containing fusion.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for selecting compounds capable of modulating an interaction between a first test agent and a second test agent, comprising:

providing a first fusion construct and a second fusion construct, said first fusion construct having an N-intein and said first test agent, said second fusion construct having a C-intein and said second test agent, wherein at least one of the two fusion constructs has an inactive reporter capable of being converted to an active reporter upon trans-splicing through said N-intein and said C-intein;

allowing said first test agent in said first fusion construct to interact with said second test agent in said second fusion construct in the presence of one or more test compounds; and detecting said active reporter.

2. The method of claim 1, wherein said first fusion construct comprises a first inactive reporter fused to the N-terminus of said N-intein, and said second fusion construct comprises a second inactive reporter fused to the C-terminus of said C-intein, and wherein said active reporter is formed upon ligation of said first and second inactive reporters.

3. The method of claim 1, wherein the first and second fusion constructs are allowed to interact with each other in vitro.

4. The method of claim 1, wherein said active reporter is detected based on molecular weight.

5. The method of claim 1, wherein said active reporter is detected by a color assay.

6. The method of claim 1, wherein said active reporter is detected by an affinity assay.

7. The method of claim 1, further comprising:

allowing said first test agent in said first fusion construct to interact with said second test agent in said second fusion construct in the absence of said compound;

detecting said active reporter; and comparing the level of said active reporter determined in the presence and absence of said compound.

8. The method of claim 2, wherein said first inactive reporter is a non-proteinaceous moiety fused to the N-terminus of said N-intein through an amino acid linker.

9. The method of claim 2, wherein said second inactive reporter is a non-proteinaceous moiety fused to the C-terminus of said C-intein through an amino acid linker selected from the group consisting of cysteine, serine, and threonine.

10. The method of claim 2, wherein said second inactive reporter is a polypeptide having an N-terminus amino acid selected from the group consisting of cysteine, serine, and threonine.

11. A method for selecting compounds capable of interfering with an interaction between a first test polypeptide and a second test polypeptide comprising:

introducing into a host cell a first chimeric gene and a second chimeric gene, said first chimeric gene encoding a first fusion protein having said first test polypeptide, an N-intein, and a first inactive reporter polypeptide fused to the N-terminus of an N-intein, said second chimeric gene encoding a second fusion protein having said second test polypeptide, a C-intein, and a second inactive reporter polypeptide fused to the C-terminus of said C-intein, wherein ligation between the C-terminus of said first inactive reporter polypeptide and the N-terminus of said second inactive reporter polypeptide forms an active reporter protein;

expressing said first fusion protein and said second fusion protein in said host cell in the presence of one or more test compounds; and determining the production of said active reporter protein, wherein the inhibition of the production of said active reporter protein would indicate that at least one of said one or more test compounds is capable of interfering with the interaction between said first test polypeptide and said second test polypeptide.

12. The method of claim 11, wherein said active reporter protein is a counterselectable reporter.

13. The method of claim 11, wherein said first inactive reporter polypeptide is an N-terminal fragment of said active reporter protein and said second inactive reporter polypeptide is the remaining C-terminal fragment of said active reporter protein.

14. The method of claim 11, wherein said host cell is an yeast cell.

15. The method of claim 11, wherein said first test polypeptide is fused to the C-terminus of said N-intein in said first fusion protein, and said second test polypeptide is fused to the N-terminus of said C-intein in said second fusion protein.

16. The method of claim 11, wherein said first test polypeptide is fused to the N-terminus of said first inactive reporter polypeptide in said first fusion protein, and said second test polypeptide is fused to the N-terminus of said C-intein in said second fusion protein.

17. The method of claim 11, wherein said first test polypeptide is fused to the C-terminus of said N-intein in said first fusion protein, and said second test polypeptide is fused to the C-terminus of said second inactive reporter polypeptide in said second fusion protein.

18. The method of claim 11, wherein said first test polypeptide is fused to the N-terminus of said first inactive reporter polypeptide in said first fusion protein, and said second test polypeptide is fused to the C-terminus of said second inactive reporter polypeptide in said second fusion protein.

19. The method of claim 11, wherein said active reporter protein is a transcription suppressor and said host cell further comprises a detectable gene that is suppressed only when said transcription suppressor is present.

20. The method of claim 11, further comprising expressing a third test polypeptide in said host cell, wherein the interaction between said first and second test polypeptide requires the presence of said third test polypeptide.

21. The method of claim 20, wherein said third test polypeptide modifies post-translationally at least one of said first and second test polypeptides.

22. The method of claim 12, wherein said active reporter protein is a protein that directly or indirectly inhibits the host cell growth.

23. The method of claim 14, wherein said yeast cell is a diploid cell and said step of introducing into said host cell said first chimeric gene and said second chimeric gene comprises mating a first haploid yeast cell having said first chimeric gene with a second haploid yeast cell having said second chimeric gene.

24. A method for selecting compounds capable of interfering with an interaction between a first test polypeptide and a second test polypeptide comprising:

introducing into a first yeast haploid cell a first chimeric gene encoding a first fusion protein having said first test polypeptide, an N-intein, and a first inactive reporter polypeptide fused to the N-terminus of an N-intein;

introducing a second chimeric gene into a second yeast haploid cell of a mating type opposite to that of said first yeast haploid cell, said second chimeric gene encoding a second fusion protein having said second test polypeptide, a C-intein, and a second inactive reporter polypeptide fused to the C-terminus of said C-intein, wherein ligation between the C-terminus of said first inactive reporter polypeptide and the N-terminus of said second inactive reporter polypeptide forms an active reporter protein that is counterselectable;

mating said first and second yeast haploid cells to form a yeast diploid cell and expressing said first fusion protein and said second fusion protein in said yeast diploid cell in the presence of one or more test compounds; and determining the production of said active reporter protein, wherein the inhibition of the production of said active reporter protein would indicate that at least one of said one or more test compounds is capable of interfering with the interaction between said first test polypeptide and said second test polypeptide.

25. The method of claim 24, wherein said active reporter protein is a toxin that inhibits the growth of said yeast diploid cell, and the production of said toxin is determined by detecting the growth of said yeast diploid cell.

26. The method of claim 24, wherein said active reporter protein is a orotidine-5'-decarboxylase encoded by URA3 gene and said expressing and determining steps are conducted while said yeast diploid cell is cultured in a medium containing 5-FOA.

* * * * *